US009181290B2

(12) United States Patent
Liu et al.

(10) Patent No.: US 9,181,290 B2
(45) Date of Patent: Nov. 10, 2015

(54) INHIBITION OF BIOFILM FORMATION BY 1,2,3,4,6-PENTA-O-GALLOYL-D-GLUCOPYRANOSE

(75) Inventors: Shih-Tung Liu, Tao-Yuan (TW);
Mei-Hui Lin, Tao-Yuan (TW);
Fang-Rong Chang, Kaohsiung (TW);
Mu-Yi Hua, Guishan Township, Taoyuan County (TW); Hung-Wei Yang, Su'ao Township, Yilan County (TW)

(73) Assignee: CHANG GUNG UNIVERSITY (TW)

( * ) Notice: Subject to any disclaimer, the term of this patent is extended or adjusted under 35 U.S.C. 154(b) by 132 days.

(21) Appl. No.: 13/236,387

(22) Filed: Sep. 19, 2011

(65) Prior Publication Data
US 2012/0321566 A1 Dec. 20, 2012

(30) Foreign Application Priority Data
Jun. 17, 2011 (TW) .............................. 100121220 A

(51) Int. Cl.
C07H 15/207 (2006.01)
C07H 13/00 (2006.01)
C07H 13/08 (2006.01)
A61K 8/60 (2006.01)
A61Q 11/00 (2006.01)
A61Q 17/00 (2006.01)
A01N 43/16 (2006.01)
A61K 31/7032 (2006.01)
A61K 9/00 (2006.01)
A61K 9/68 (2006.01)

(52) U.S. Cl.
CPC .............. C07H 13/08 (2013.01); A01N 43/16 (2013.01); A61K 8/60 (2013.01); A61K 31/7032 (2013.01); A61Q 11/00 (2013.01); A61Q 17/005 (2013.01); A61K 9/006 (2013.01); A61K 9/0014 (2013.01); A61K 9/0056 (2013.01); A61K 9/0058 (2013.01)

(58) Field of Classification Search
USPC .................. 536/18.1, 18.2, 119, 115; 514/25; 510/108
See application file for complete search history.

(56) References Cited

U.S. PATENT DOCUMENTS

| | | | |
|---|---|---|---|
| 7,691,418 B2 | 4/2010 | Rossel | |
| 8,512,731 B2 | 8/2013 | Yang et al. | |
| 8,617,523 B2 | 12/2013 | Trivedi et al. | |
| 2003/0153983 A1 | 8/2003 | Miller et al. | |
| 2003/0171421 A1 | 9/2003 | Davies et al. | |
| 2006/0058243 A1 | 3/2006 | Chen et al. | |
| 2007/0282422 A1* | 12/2007 | Biggs et al. | 623/1.13 |
| 2008/0149299 A1 | 6/2008 | Slaughter | |
| 2008/0249299 A1 | 10/2008 | Ren et al. | |
| 2009/0192192 A1 | 7/2009 | Ammendola et al. | |
| 2009/0255536 A1 | 10/2009 | Av-Gay et al. | |
| 2009/0304621 A1 | 12/2009 | Cavitt et al. | |
| 2010/0087769 A1 | 4/2010 | Bukshpan et al. | |
| 2010/0152101 A1 | 6/2010 | Reid | |
| 2010/0285084 A1 | 11/2010 | Yang et al. | |
| 2010/0298208 A1 | 11/2010 | Cohen et al. | |
| 2011/0008402 A1 | 1/2011 | Madhyastha et al. | |
| 2011/0076312 A1 | 3/2011 | Pokropinski, Jr. et al. | |
| 2011/0076332 A1 | 3/2011 | Yu et al. | |
| 2011/0086101 A1 | 4/2011 | Madhyastha et al. | |
| 2011/0135621 A1 | 6/2011 | Miller et al. | |

FOREIGN PATENT DOCUMENTS

| | | |
|---|---|---|
| WO | 2008/132718 A2 | 11/2008 |
| WO | 2010/072257 A1 | 7/2010 |
| WO | 2010/112848 A2 | 10/2010 |
| WO | 2010/144686 A1 | 12/2010 |

OTHER PUBLICATIONS

Lin et al. "Inhibitory Effects of 1,2,3,4,6-Penta-O-Galloyl-beta-D-glucopyranose on Biofilm Formation by *Staphylococcus aureus*", Antimicrobial Agents and Chemotherapy, vol. 55, No. 3, Mar. 2011 pp. 1021-1027.*
Royal Society of Chemistry, Biofilms Under Control, pp. 1-2, Feb. 2009.*
Ammons, Mary Cloud B. et al., "Anti-biofilm efficacy of a lactoferrin/xylitol wound hydrogel used in combination with silver wound dressings," International Wound Journal, 2011, vol. 8, No. 3, pp. 268-273.
Aslam et al., "Combination of Tigecycline and N-Acetylcysteine Reduces Biofilm-Embedded Bacteria on Vascular Catheters," Antimicrobial Agents and Chemotherapy, Apr. 2007, vol. 51, No. 4, pp. 1556-1558.
Beckloff et al., "Activity of an Antimicrobial Peptide Mimetic against Planktonic and Biofilm Cultures of Oral Pathogens," Antimicrobial Agents and Chemotherapy, Nov. 2007, vol. 51, No. 11, pp. 4125-4132.
Brady et al., "Osteomyelitis and the role of biofilms in chronic infection," FEMS Immunology & Medical Microbiology, Jan. 2008, vol. 52, issue 1, pp. 13-22.
Burton et al. "Antibiofilm Activity of GlmU Enzyme Inhibitors against Catheter-Associated Uropathogens," Antimicrobial Agents and Chemotherapy, May 2006, vol. 50, No. 5, pp. 1835-1840.
Carlson et al., "Anti-biofilm properties of chitosan-coated surfaces," Journal of Biomaterials Science: Polymer Edition, 2008, vol. 19, issue 8, pp. 1035-1046.
Chen, Fu et al., "Triclosan-Loaded Tooth-Binding Micelles for Prevention and Treatment of Dental Biofilm," Pharmaceutical Research, 2010, vol. 27, pp. 2356-2364.
Corrigan et al., "The role of *Staphylococcus aureus* surface protein SasG in adherence and biofilm formation," Microbiology, 2007, vol. 153, pp. 2435-2446.
Cramton et al., "The Intercellular Adhesion (ica) Locus Is Present in *Staphylococcus aureus* and Is Required for Biofilm Formation," Infection and Immunity, 1999, vol. 67, No. 10, pp. 5427-5433.

(Continued)

Primary Examiner — Lezah Roberts
(74) Attorney, Agent, or Firm — Kilpatrick Townsend & Stockton LLP

(57) ABSTRACT

Disclosed herein are an anti-biofilm composition and a method to inhibit or prevent cell adhesion and/or biofilm formation by a microorganism, in which use of 1,2,3,4,6-penta-O-galloyl-D-glucopyranose (PGG) is involved therein.

19 Claims, 9 Drawing Sheets

(56) References Cited

OTHER PUBLICATIONS

Darouiche et al., "Antimicrobial and antibiofilm efficacy of triclosan and DispersinB combination," Journal of Antimicrobial Chemotherapy, 2009, vol. 64, pp. 88-93.
de Carvalho, "Biofilms: Recent Developments on an Old Battle," Recent Patents on Biotechnology, 2007, vol. 1, pp. 49-57.
Definition of Pseudomonas aeruginosa as defined by Wikipedia.org (http://en.wikipedia.org/wiki/Pseudomonas_aeruginosa) 17 pages.
Definition of Streptococcus mutans as defined by Wikipedia.org (http://en.wikipedia.org/wiki/Streptococcus_mutans) 12 pages.
Goetz, "Staphylococcus and biofilms," Molecular Microbiology, 2002, vol. 43, issue 6, pp. 1367-1378.
Hall-Stoodley et al., "Characterization of biofilm matrix, degradation by DNase treatment and evidence of capsule downregulation in Streptococcus pneumoniae clinical isolates," BMC Microbiology, Oct. 2008, vol. 8, pp. 173.
Heilmann et al., "Characterization of Tn917 insertion mutants of Staphylococcus epidermidis affected in biofilm formation," Infection and Immunity, Jan. 1996, vol. 64, No. 1, pp. 277-282.
Hu et al., "Penta-1, 2, 3, 4, 6-O-galloyl-β-d-glucose induces p53 and inhibits STAT3 in prostate cancer cells in vitro and suppresses prostate xenograft tumor growth in vivo," Molecular Cancer Therapeutics, Sep. 2008, vol. 7, issue 9, pp. 2681-2691.
Itoh et al., "Depolymerization of β-1,6-N-Acetyl-D-Glucosamine Disrupts the Integrity of Diverse Bacterial Biofilms," Journal of Bacteriology, Jan. 2005, vol. 187, No. 1, pp. 382-387.
Lewis, "Riddle of Biofilm Resistance," Antimicrobial Agents and Chemotherapy, 2001, vol. 45, No. 4, pp. 999-1007.
Maki et al. "Engineering out the risk for infection with urinary catheters," Emerging Infectious Diseases, Mar.-Apr. 2001, vol. 7, No. 2, pp. 342-347.
O'Neill et al., "Carriage of both the fnbA and fnbB genes and growth at 37° C. promote FnBP-mediated biofilm development in meticillin-resistant Staphylococcus aureus clinical isolates," Journal of Medical Microbiology, 2009, vol. 58, pp. 399-402.
Perez-Giraldo et al., "Influence of N-acetylcysteine on the formation of biofilm by Staphylococcus epidermidis," Journal of Antimicrobial Chemotherapy, 1997, vol. 39, pp. 643-646.
Raad et al., "Anti-adherence activity and antimicrobial durability of anti-infective-coated catheters against multidrug-resistant bacteria," Journal of Antimicrobial Chemotherapy, 2008, vol. 62, pp. 746-650.
Rosenstein et al., "Genome Analysis of the Meat Starter Culture Bacterium Staphylococcus carnosus TM300," Applied and Environmental Microbiology, Feb. 2009, vol. 75, No. 3, pp. 811-822.
Schlag et al., "Inhibition of Staphylococcal Biofilm Formation by Nitrite," Journal of Bacteriology, Nov. 2007, vol. 189, No. 21, pp. 7911-7919.
Stary et al., "New Architectures for Tet-On and Tet-Off Regulation in Staphylococcus aureus," Applied Environmental Microbiology, 2010, vol. 76, No. 3, pp. 680-687.
Tormo et al., "Bap-dependent biofilm formation by pathogenic species of Staphylococcus: evidence of horizontal gene transfer?", Microbiology, 2005, vol. 151, pp. 2465-2475.
Wei et al., "Effect of MUC7 peptides on the growth of bacteria and on Streptococcus mutans biofilm," Journal of Antimicrobial Chemotherapy, Jun. 2006, vol. 57, issue 6, pp. 1100-1109.
Wu et al., "Lysostaphin Disrupts Staphylococcus aureus and Staphylococcus epidermidis Biofilms on Artificial Surfaces," Antimicrobial Agents and Chemotherapy, 2003, vol. 47, No. 11, pp. 3407-3414.
Ymele-Leki et al., "Erosion from Staphylococcus aureus Biofilms Grown under Physiologically Relevant Fluid Shear Forces Yields Bacterial Cells with Reduced Avidity to Collagen," Applied Environmental Microbiology, 2007, vol. 73, No. 6, pp. 1834-1841.
Zhang et al., "Anti-Cancer, Anti-Diabetic and Other Pharmacologic and Biological Activities of Penta-Galloyl-Glucose," Pharmaceutical Research, Sep. 2009, vol. 26, issue 9, pp. 2066-2080.

\* cited by examiner 60 min    PGG(μM)
Polystyrene  Polycarbonate

INHIBITION OF BIOFILM FORMATION BY 1,2,3,4,6-PENTA-O-GALLOYL-D-GLUCOPYRANOSE

CROSS-REFERENCE TO RELATED APPLICATION

This application claims priority of Taiwanese Application No. 100121220, filed on Jun. 17, 2011.

BACKGROUND OF THE INVENTION

1. Field of the Invention

This invention primarily relates to a method to prevent or inhibit cell adhesion and/or biofilm formation by a microorganism, in which use of 1,2,3,4,6-penta-O-galloyl-D-glucopyranose (PGG) is involved therein.

2. Description of the Related Art

Nearly 99% of the microorganisms living in this planet thrive in microbial communities known as biofilms. They are formed by adhesion of cells to surfaces through an exopolymeric matrix. This matrix is important both in the formation and structure of the biofilm, and also to the protection of the cells since it may prevent the access of antimicrobials and xenobiotics to the cells inside the biofilm and confer protection against environmental stresses such as UV radiation, pH shifts, osmotic shock and desiccation. Fossilised biofilms of up to 3.5 billion years are among the oldest records of life on Earth. Biofilms are the planet's most successful form of colonialism as they live on soils, sediments, mineral, plant and animal surfaces, even under extreme environments, from glaciers to hot vents. Biofilms are even able to thrive in highly irradiated areas of nuclear power plants.

Cell aggregation is advantageous and required in several processes, namely in biological wastewater treatment and bioremediation systems. However, they constitute a serious problem in many industrial processes (e.g., paper, food, cosmetic and pharmaceutical industries) because they can cause corrosion and limit mass and heat transfer in pipes and tubes and mainly in water distribution systems and healthcare environments as they are a source of microbial infections. Furthermore, biofilms can also bioaccumulate metals and toxic compounds. Biofilms can contaminate contact lenses, catheters, endotracheal tubes, mechanical cardiac valves, prosthetic joints, surgical sutures, etc. Biofilms can result in surgical site infections, and cells in biofilms have higher resistance to antibiotics and biocides than planktonic cells and gene transfer is possible horizontally, which improves the exchange of genes between resistant and non-resistant strains.

Bacterial strains that do not produce exopolymeric substances (EPS) present lower adherent abilities than slime-producing strains. EPS is particularly valuable after the initial phase of adhesion in organisms, conferring protection against phagocytosis, interference with the cellular immune response and reduction of antibiotic potency. In fact, the host immune system is, in general, capable of rapidly killing non-adherent bacteria. The slow growth rate observed in biofilms and/or transport limitations of nutrients, metabolites and oxygen between the surface and the interior of the biofilm could be responsible for an increased antibiotic resistance over planktonic cells. Furthermore, the EPS matrix acts as an anchor, securing the cells and preventing their detachment under flow conditions, although detachment of cells may also be an important process for propagation and formation of new colonies.

The above is an excerpt from a review article, namely Carla C. C. R. de Carvalho (2007), *Recent Patents on Biotechnology*, 1, 49-57, which provides a thorough discussion of a number of scientific literatures and patent documents in relation to the prevention and control of biofilm proliferation in medical devices and water supply systems, as well as the development on anti-microbial surfaces, detergents and biocides. This review article and the references referred to therein are incorporated herein by reference in their entirety.

Biofilms can colonize on almost all surfaces, from glass to steel, and from cellulose to silicone, which are the main materials used to produce medical devices. Bacterial biofilms are frequently found in clinical and medical environments, and according to statistics, 65 percent of bacterial infections are associated with biofilms formed by bacteria. Many clinically important pathogens, such as *Staphylococcus aureus, Pseudomonas aeruginosa, Streptococci*, etc., have the ability to form biofilm. Inasmuch as bacteria living in biofilm have higher resistance to the attack of the host immune system and the toxic effect of antibiotics, it becomes difficult to treat infections of this kind. In particular, it is extremely hard to eradicate a bacterial biofilm once formed in an implanted medical device such as a cardiac catheter, a urethral catheter, a prosthetic joint, an artificial heart valve, an artificial blood vessel, etc., and replacing the biofilm-contaminated device with a new one is imperative, which leads to a year-by-year rise in medical expenses.

Amongst pathogens that cause nosocomial infections, *Staphylococcus aureus* is of great concern. *Staphylococcus aureus* forms biofilms on medical devices and causes pneumonia, meningitis, endocarditis, osteomyelitis and septicemia (Friedrich Götz (2002), *Mol. Microbiol.*, 43 (6):1367-1378). Formation of biofilm by *S. aureus* is closely associated with the synthesis of an extracellular polysaccharide substance (EPS), namely polysaccharide intercellular adhesion (PIA), which is a β-1,6-linked N-acetyl (succinyl) glucosamine polymer synthesized by enzymes encoded by an ica operon (Sarah E. Cramton et al. (1999), *Infect. Immun.*, 67 (10):5427-5433). In addition, the proteins of *S. aureus* that contribute to biofilm formation include fibronectin-binding proteins A and B (Eoghan O'Neill et al. (2009), *J. Med. Microbiol.*, 58:399-402), collagen-binding protein (Patrick Ymele-Leki and Julia M. Ross (2007), *Appl. Environ. Microbiol.*, 73 (6):1834-1841), SasG surface protein (Rebecca M. Corrigan et al. (2007), *Microbiology*, 153:2435-2446), and the biofilm associated protein bap (M. Ángeles Tormo et al. (2005), *Microbiology*, 151:2465-2475). Meanwhile, the pertinacious form of biofilm formation is inhibited by extracellular proteases produced by the organism (Elena Stary et al. (2010), *Appl. Environ. Microbiol.*, 76 (3):680-687). These reports illustrate that factors on the bacterial surface facilitate attachment of bacteria and establishment of multilayered cell clusters on a solid surface, which are crucial to biofilm formation (Friedrich Götz (2002), supra). Owing to high resistance to antibiotics of biofilm-imbedded staphylococci (Kim Lewis (2001), *Antimicrob, Agents Chemother.*, 45 (4):999-1007), biofilm-associated infections are extremely difficult to treat, necessitating the development of drugs that prevent and destroy biofilm.

In the last two decades, numerous investigators specializing in the research and development of anti-biofilm drugs and anti-biofilm medical instruments have identified several substances useful for preventing the formation or removal of staphylococcal biofilms. For example, lysostaphin, which is a peptidoglycan-degrading enzyme, prevents staphylococcal biofilm formation (Julie A. Wu et al. (2003), *Antimicrob. Agents Chemother.*, 47 (11):3407-3414); N-acetylcysteine (NAC), which is a clinical drug, reduces EPS production, subsequently inhibiting biofilm formation (C. Pérez-Giraldo et al. (1997), *J. Antimicrob. Chemother.*, 39:643-646); iodoacetamide (IDA) and N-ethyl maleimide (NEM), which are inhibitors of N-acetyl-D-glucosamine-1-phosphate acetyltransferase that catalyzes the biosynthesis of UDP-N-acetylglucosamine, i.e., a precursor of PIA, also inhibit biofilm formation (Euan Burton et al. (2006), *Antimicrob. Agents Chemother.*, 50:1835-1840); and dispersin B, which hydrolyzes β-1,6-N-acetyl-glucosamine, disperses mature biofilm and is an agent potentially useful in anti-biofilm therapy (Yoshikane Itoh et al. (2005), *J. Bacteriol.*, 187 (1):382-7). In addition, there have been researches investigating the use of different clinical antibiotics in combination to inhibit bacterial biofilm formation (Euan Burton et al. (2006), supra; and Saima Aslam et al. (2007), *Antimicrob. Agents Chemother.*, 51 (4):1556-8).

While the target drugs or candidate drugs studied in the earlier reports are considered to have potential as an anti-biofilm agent (Saima Aslam et al. (2007), supra; Nicholas Beckloff et al. (2007), *Antimicrob. Agents Chemother.*, 51 (11):4125-32; Ross P. Carlson et al. (2008), *J. Biomater. Sci. Polymer Ed.*, 19 (8): 1035-1046; I. Raad et al. (2008), *J. Antimicrob. Chemother.*, 62:746-650; Prabha Ramritu et al. (2008), *Am. J. Infect. Control*, 36 (2) 104-117; and Guo-Xian Wei et al. (2006), *J. Antimicrob. Chemother.*, 57:1100-9), the greatest concern for enzymatic drugs to be used in clinic is the extremely high cost thereof, and drugs exhibiting bacterial-killing effect(s) are liable to induce resistant strains. Furthermore, the clinical efficacies of these target drugs or candidate drugs as studied in the above reports have yet to be verified.

There also exist numerous published patent documents disclosing a diversity of approaches to inhibit or prevent biofilm formation on various surfaces, including, e.g., WO 2008/132918 A2, WO 2010/072257 A1, WO 2010/112848 A2, WO 2010/144686 A1, U.S. Pat. No. 7,691,418 B2, US 20100152101 A1 (corresponding to TW200913996A), US 20090192192 A1, US 20090255536 A1, US 20090304621 A1, US 20100087769 A1, US 20100285084 A1, US 20100298208 A1, US 20110008402 A1, US 20110076312 A1, US 201100763332 A1, and US 20110086101 A1. These patent documents are incorporated herein by reference in their entirety.

In order to exploit anti-biofilm agents that are effective at low concentrations, non-toxic and biodegradable, health and environment friendly, and cost-saving, the applicants screened forty eight compounds isolated from plants commonly used in Chinese medicine, and surprisingly found that 1,2,3,4,6-penta-O-galloyl-β-D-glucopyranose (β-PGG), either in a solution or coated on solid surfaces, did not inhibit the growth of tested microorganisms, yet prevented biofilm formation on solid surfaces. The α-anomer of β-PGG was also found to exhibit similar anti-biofilm effect. It is contemplated that PGG, either in the β-form or the α-form or a mixture of the α- and β-forms, may act as a potent anti-biofilm agent.

SUMMARY OF THE INVENTION

Therefore, in a first aspect, this invention provides an anti-biofilm composition, comprising 1,2,3,4,6-penta-O-galloyl-D-glucopyranose (PGG).

In a second aspect, this invention provides a method to prevent or inhibit adhesion and/or biofilm formation by a microorganism, comprising applying to a site in need of such treatment a composition containing PGG.

BRIEF DESCRIPTION OF THE DRAWINGS

The above and other objects, features and advantages of this invention will become apparent with reference to the following detailed description and the preferred embodiments taken in conjunction with the accompanying drawings, in which.

DETAILED DESCRIPTION OF THE INVENTION

Figure 1:
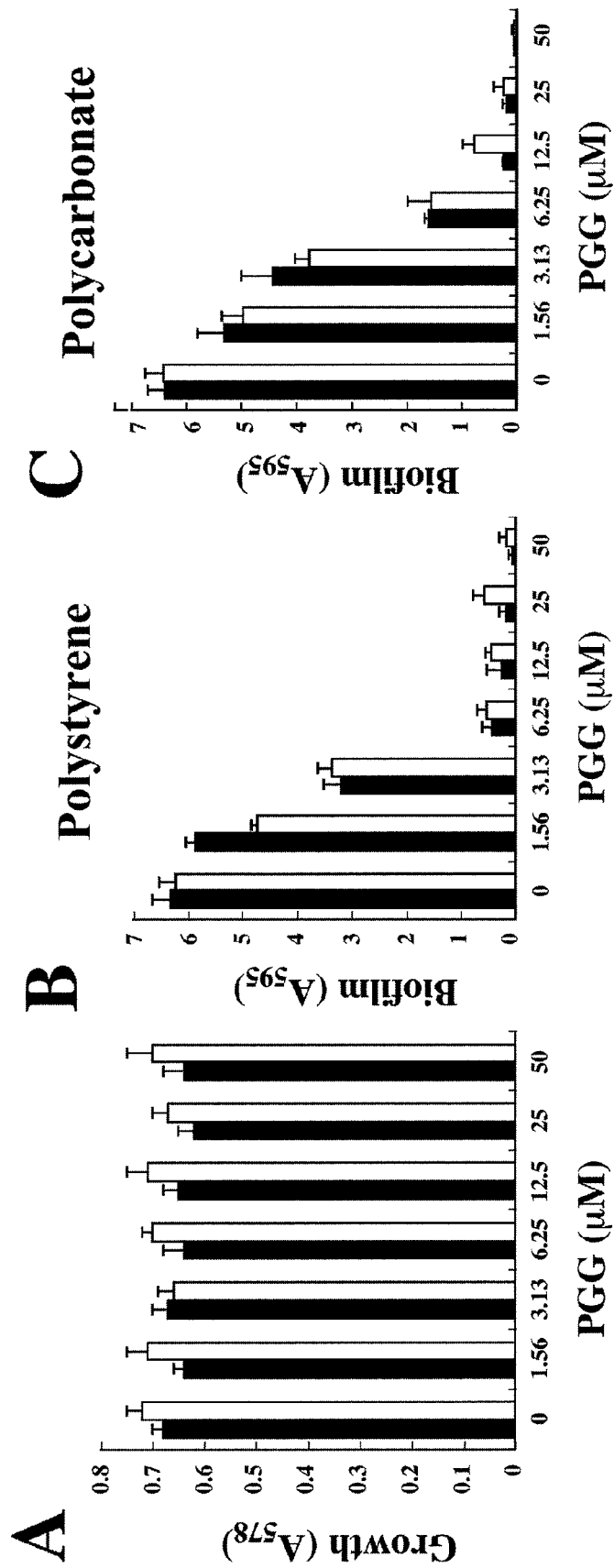
FIG. 1 shows the effects of 1,2,3,4,6-penta-O-galloyl-β-D-glucopyranose (β-PGG) upon bacterial growth (panel A) and biofilm formation on polystyrene surface (panel B) and polycarbonate surface (panel C) by *S. aureus* SA113 (ATCC 35556) after incubation at 37° C. for 6 hrs (black bar) or 24 hrs (white bar), in which the cell density was determined by measuring the absorbance at 578 nm ($A_{578}$); the amounts of biofilm were quantified by crystal violet staining, with the amount of biofilm formed by untreated bacterial cells being set as 100%; each experiment was repeated three times, with n=6 for each sample tested; and error bar represents standard deviation.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the words "comprises," "contain" and variants thereof have a corresponding meaning.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described. For clarity, the following definitions are used herein.

As used herein, the term "biofilm" refers to communities of microorganisms that are attached to a substrate or surface. The microorganisms often excrete a protective and adhesive matrix of polymeric compounds. They often have structural heterogeneity, genetic diversity, and complex community interactions.

As used herein, the term "biofilm-forming microorganism" refers to any microorganism that forms a biofilm during colonization and proliferation on a surface. The environment may comprise any biofilm-forming microorganism selected from bacteria, fungi, yeast, viruses and protozoa.

The biofilm-forming microorganism may be a bacterial pathogen that is Gram-positive or Gram-negative and derived from a bacterial species selected from the group consisting of: *Staphylococcus* sp., e.g., *Staphylococcus aureus, Staphylococcus epidermidis, Staphylococcus epitkonidis, Staphylococcus agalactiae* and *Staphylococcus saprophyticus, Staphylococcus haemolyticus, Staphylococcus warneri, Staphylococcus hominis, Staphylococcus simulans, Staphylococcus lugdunensis, Staphylococcus schleiferi, Staphylococcus capitis, Staphylococcus caprae, Staphylococcus pasteuri, Staphylococcus cohnii, Staphylococcus xylosus,* and *Staphylococcus saccharolyticu,* and combinations thereof; *Enterococcus* sp., e.g., Vancomycin-resistant Enterococci (VRE), *Enterococcus faecalis, Enterococcus cloacae; Acinetobacter baumannii; Streptococcus* sp., e.g., *Streptococcus* Group A or B or C, *Streptococcus pyogenes, Streptoccocus pneumoniae; Streptococcus viridans; Pseudomonas* sp., e.g., *Pseudomonas aeruginosa; Escherichia coli; Helicobacter* sp., e.g., *Helicobacter pylori; Chlamydia* sp., e.g., *Chlamydia trachomatis, Chlamydia pneumoniae, Chlamydia psittaci; Clostridia* sp., e.g., *Clostridium botulinum; Haemophilus* sp., e.g., *Haemophilus influenzae; Shigella* sp., e.g., *Shigella flexneri; Bacillus* sp., e.g., *Bacillus anthracis; Neisseria* sp., e.g., *Neisseria gonorrhea, Neisseria meningitidis; Mycobacterium* sp., e.g., *Mycobacterium tuberculosis; Francisella fularensis; Klebsiella* sp., e.g., *Klebsiella pneumoniae, Klebsiella oxytoca; Yersinia* sp., e.g., *Yersinia pestis; Propionibacterium* sp., e.g., *Propionibacterium acnes; Burkholderia* sp., e.g., *Burkholderia cepacia, Burkholderia mallei* and *B pseudomallei; Treponema* sp., e.g., *Treponema denticola; Enterobacter* sp., e.g., *Enterobacter cloacae; Borrelia burgdorferi; Proteus mirabilis; Providentia sturtii; Serratia marcescens; Fusobacterium nucleatum; Aggregatibacter cictinontycetemcomitans* (formerly *Actinobacillus actinomycetemcomitans*); *Salmonella* sp.; *Listeria* sp.; *Campylobacter* sp.; *Bacteriodes* sp.; *Prevotella* sp.; *Corynebacterium* sp.; *Porphyromonas* sp.; and *Peptostreptococcus* sp.

In particular, the bacterial pathogen is derived from a bacterial species selected from the group consisting of: *Staphylococcus* sp., for example *Staphylococcus aureus* and *Staphylococcus epidermidis; Enterococcus faecalis; Acinetobacter baumannii; Pseudomonas* sp., for example *Pseudomonas aeruginosa; Propionibacterium* sp., for example *Propionibacterium acnes; Haemophilus* sp., for example *Haemophi-*

*lus influenza*; *Burkholderia* sp., for example *Burkholderia cepacia*; and *Streptococcus* sp. Preferably the bacterium is selected from *Staphylococcus* sp., for example *Staphylococcus aureus* and *Staphylococcus epidermidis*; *Enterococcus faecalis*; *Acinetobacter baumannii*; and *Pseudomonas* sp., for example *Pseudomonas aeruginosa*.

The biofilm-forming microorganism may be a viral pathogen derived from a virus selected from the group consisting of: human immunodeficiency virus (HTVI & 2); human T Cell leukemia Virus (HTLV 1 & 2); Ebola virus; human papilloma virus (e.g., HPV-2, HPV-5, HPV-8 HPV-16, HPV-18, HPV-31, HPV-33, HPV-52, HPV-54 and HPV-56); papovavirus; rhinovirus; poliovirus; herpesvirus; adenovirus; Epstein Barr virus; influenza virus, hepatitis B and C viruses, Variola virus, rotavirus or SARS coronavirus.

The biofilm-forming microorganism may be a parasitic pathogen derived from a parasitic species selected from the group consisting of *Trypanosoma* sp. (*Trypanosoma cruzi*, *Trypansosoma brucei*), *Leishmania* sp., *Giardia* sp., *Trichomonas* sp., *Entamoeba* sp., *Naegleria* sp., *Acanthamoeba* sp., *Schistosoma* sp., *Plasmodium* sp., *Crytosporidiwn* sp., *Isospora* sp., *Balantidium* sp., *Loa loa*, *Ascaris lumbricoides*, *Dirofilaria immitis*, *Toxoplasma* sp., e.g *Toxoplasma gondii*.

The biofilm-forming microorganism may be a fungal pathogen derived from a fungal species selected from the group consisting of *Absidia* sp., *Acremonium* sp., *Actinomadura* sp., *Apophysomyces* sp., *Arthrographis* sp., *Aspergillus* sp., *Basidiobolus* sp., *Beauveria* sp., *Blastomyces* sp., *Blastoschizomyces* sp., *Candida* sp. (e.g., *Candida albicans*, *Candida parapsilosis* and *Candida utilis*), *Chrysosporium* sp., *Cladophialophora* sp., *Coccidioides* sp., *Conidiobolus* sp., *Cryptococcus* sp., *Cunninghamella* sp., *Emmonsia* sp., *Epidermophyton* sp., *Exophiala* sp., *Fonsecaea* sp., *Fusarium* sp., *Geotrichum* sp., *Graphium* sp., *Histoplasma* sp., *Lacazia* sp., *Leptosphaeria* sp., *Malassezia* sp., *Microsporiim* sp., *Mucor* sp., *Neotestudina* sp., *Nocardia* sp., *Nocardiopsis* sp., *Paecilomyces* sp., *Paracoccidiomyces* sp., *Phialophora* sp., *Phoma* sp., *Piedraia* sp., *Pneumocystis* sp., *Pseudallescheria* sp., *Pyrenochaeta* sp., *Rhizomucor* sp., *Rliizopus* sp., *Rhodotorula* sp., *Saccharomyces* sp., *Scedosporium* sp., *Scopulariopsis* sp., *Sporobolomyces* sp., *Sporotrix* sp., *Syncephalastrum* sp., *Tinea* sp., *Trichoderma* sp., *Trichophyton* sp. (e.g, *Trichophyton rubrum* and *Trichophyton interdigitale*), *Trichosporon* sp., *Ulocladium* sp., *Ustilago* sp., *Verticillium* sp., and *Wangiella* sp.

As used herein, the terms "anti-biofilm," "biofilm inhibiting," "biofilm preventing" or "biofilm reducing" or "biofilm removing" refer to the prevention of biofilm formation, inhibition of the establishment or growth of a biofilm, or decrease in the amount of microorganisms that attach and/or grow upon a substrate, up to and including the complete removal of the biofilm.

As used herein, the term "anti-biofilm agent" refers to any element, chemical, biochemical or the like that is effective against cell adherence or the formation of biofilms or agglomerate caused by the adhering microorganisms.

As used herein, the term "site" means a "surface" or a "substrate." The term "substrate" includes any living or non-living structure on which a biofilm can form or has formed. For example, biofilms often grow on synthetic materials submerged in an aqueous solution or exposed to humid air, and can also form as floating mats on a liquid surface, in which case the microorganisms are adhering to each other or to the adhesive matrix characteristic of a biofilm. Substrate includes, but is not limited to, hard or soft surfaces such as polymers, plastics, tubing, ceramics, cellulosic materials (e.g., wood and paper), metals, glass, concrete, hydroxyapatite, skin, bone, or tissues.

As used herein, the term "surface" refers to any surface whether in an industrial or a medical setting that provides an interface between an object and a fluid, permitting at least intermittent contact between the object and the fluid. A surface, as understood herein, further provides a plane whose mechanical structure, without further treatment, is compatible with the adherence of microorganisms. Surfaces compatible with biofilm formation may be smooth or irregular. Fluids contacting the surfaces can be stagnant or flowing, and can flow intermittently or continuously, with laminar or turbulent or mixed rheologies. A surface upon which a biofilm forms can be dry at times with sporadic fluid contact, or can have any degree of fluid exposure including total immersion. Fluid contact with the surface can take place via aerosols or other means for air-borne fluid transmission.

Biofilm formation with health implications can involve those surfaces in many environments, including surfaces found in medical environments and those surfaces in industrial or residential environments that are involved in those functions essential to well-being like nutrition, sanitation and the prevention of disease. By reference to industrial and residential settings, biofilm formation on contact-items where microorganisms can infect by skin-surface contact is an area of concern.

Biofilm formation can be evident on the surfaces of household items, including: flooring, e.g., vinyl, laminate, wood, stone, carpeting (wool, synthetic, polyester, polypropylene, etc.), tile, etc.; walls, e.g., drywall, wallpaper, paints, etc.; furniture, e.g., plastics, woods, laminates, ceramics, metals, glass, upholsteries, etc.; toys, e.g., plastics, woods, ceramics, cloth, metals, glass, etc.; appliances, e.g., toasters, microwave ovens, conventional ovens, washers, dryers, dishwashers, mixers, food processors, etc.; electronic appliances, e.g., DVRs, DVD players, televisions, computers, keyboards, mice, cable boxes, remote controllers, MP3 players, stereo systems, etc.; communication devices, e.g., phones, earpieces for phones, etc.; kitchen fixtures, e.g., sinks and associated hardware, faucets, etc.; bathroom fixtures, e.g., baths and associated hardware, showers and associated hardware, sinks and associated hardware, faucets, toilets and associated hardware, shower curtains or liners, etc.; electrical switch plates and outlets; lighting; doors and associated hardware; railings and associated posts; trash cans; and other surfaces found in homes.

Similarly, biofilm formation may be encountered on surfaces of commonly visited public places. Such surfaces may negatively impact the health of an individual who contacts the biofilm by skin contact. Such public use surfaces include: laundry, shopping carts, shelving, cash registers, key pads commonly used for credit card purchases, touch screens and other electronic equipment, conveyor belts, playground equipment, public drinking fountains, flooring (e.g., carpet or otherwise), walls, public restrooms (e.g., urinals, toilets, sinks, hand dryers (e.g., paper, cloth and air), faucets, walls and flooring contained therein, stalls, toilet paper dispensers, trash containers, feminine hygiene containers, dispensing machines, soap dispensers, etc.), railings and their associated posts, and other similar surfaces.

Biofilm formation may occur on other everyday residential and industrial items. Surfaces of residential and industrial items include: a ship hull or a portion thereof, water pipes, swimming pools, cooling towers, heat exchangers, vehicles (interior and exterior), car seats, lawn maintenance equipment (e.g., lawn mowers, edgers, clippers, weed-wackers, etc.), gardening equipment (e.g., shovels, spades, etc.), industrial equipment, tools both residential and industrial (e.g., wrenches, screwdrivers, drills, vices, etc.), concrete structures, and other items used in residential and industrial settings composed of metals, woods, glass, ceramics, plastics, polymers, waxes, liquids, etc.

Surfaces found in medical environments include the inner and outer surfaces of various instruments and devices, whether disposable or intended for repeated use. Examples include the entire spectrum of articles adapted for medical use, including scalpels, needles, scissors and other devices used in invasive surgical, therapeutic or diagnostic procedures, implantable medical devices (including artificial blood vessels, catheters and other devices for the removal or delivery of fluids to patients), artificial hearts, artificial kidneys, orthopedic pins, plates and implants, catheters and other tubes (including urological, biliary, and endotracheal tubes, peripherally insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts), prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, etc. Other examples will be readily apparent to practitioners in these arts.

Surfaces found in the medical environment include also the inner and outer surfaces of pieces of medical equipment, medical gear worn or carried by personnel in the health care setting. Such surfaces can include countertops and fixtures in areas used for medical procedures or for preparing medical apparatus, tubes and canisters used in respiratory treatments, including the administration of oxygen, of solubilized drugs in nebulizers and of anesthetic agents. Also included are those surfaces intended as biological barriers to infectious organisms in medical settings, such as gloves, aprons and face shields. Commonly used materials for biological barriers may be latex-based or non-latex based. Vinylic materials, similar to the polymerized form of the present invention, are commonly used for non-latex surgical gloves. Other such surfaces can include handles and cables for medical or dental equipment not intended to be sterile. Additionally, such surfaces include those non-sterile external surfaces of tubes and other apparatus found in areas where blood or body fluids or other hazardous biomaterials are commonly encountered.

Surfaces in contact with liquids are particularly prone to biofilm formation, and may include those reservoirs and tubes used for delivering humidified oxygen to patients. Dental unit waterlines similarly can bear biofilms on their surfaces, providing a reservoir for continuing contamination of the system of flowing and aerosolized water used in dentistry.

Other surfaces related to health include the inner and outer surfaces of those articles involved in water purification, water storage and water delivery, and those articles involved in food processing. Inasmuch as surfaces amenable to biofilm formation are vast and many, any other surfaces not specifically named above would be apparent to one skilled in the art.

According to this invention, the term "medical device" refers to a non-naturally occurring object that is inserted or implanted in a subject or applied to a surface of a subject. Medical devices can be made of a variety of biocompatible materials including metals, ceramics, polymers, gels, and fluids not normally found within the human body. Medical devices can also be fabricated using certain naturally-occurring materials or treated naturally-occurring materials. As an example, a heart valve can be fabricated by combining a treated porcine heart valve with an affixation apparatus using artificial materials. Medical devices can include any combination of artificial materials, combinations selected because of the particular characteristics of the components. For example, a hip implant can include a combination of a metallic shaft to bear the weight, a ceramic artificial joint and a polymeric glue to affix the structure to the surrounding bone. An implantable device is one intended to be completely imbedded in the body without any structure left outside the body (e.g., heart valve). An insertable device is one that is partially imbedded in the body but has a part intended to be external (e.g., a catheter or a drain). Medical devices can be intended for short-term or long-term residence where they are positioned. A hip implant is intended for several years of use, for example. By contrast, a tissue expander may only be needed for a few months, and is removed thereafter. Insertable devices tend to remain in place for shorter times than implantable devices, in part because they come into more contact with microorganisms that can colonize them.

According to this invention, an "implant" refers to any object intended for placement in a human body that is not a living tissue. Implants include naturally derived objects that have been processed so that their living tissues have been devitalized. As an example, bone grafts can be processed so that their living cells are removed, and so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human body.

Plant materials containing 1,2,3,4,6-penta-O-galloyl-β-D-glucopyranose (β-PGG) have been used frequently in treating inflammation in Chinese medicine. β-PGG has a chemical structure as shown below, and it may be dissolved in water or water-based solutions (such as saline, phosphate buffered saline, etc.), alcohols such as methanol and ethanol, and organic solvents (such as dimethyl sulfoxide (DMSO), acetone and ethyl acetate), etc.

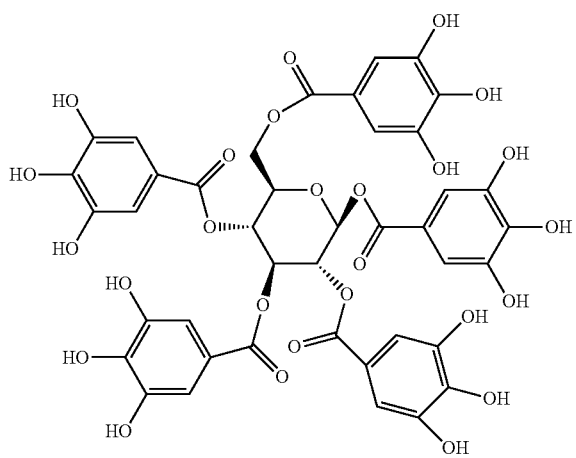

1,2,3,4,6-Penta-O-galloyl-β-D-glucopyranose (β-PGG)

β-PGG has been found to be an active anti-oxidative ingredient in geranium (Xiangshu Piao et al. (2008), *Phytother. Res.*, 22:534-538). In addition to inducing p53 expression and inhibiting STAT3 in prostate cancer cells, β-PGG suppresses the growth of prostate xenograft tumor in a nude mouse model (Hongbo Hu et al. (2008), *Mol. Cancer Ther.*, 7 (9): 2681-2691). β-PGG is also a vasorelaxant that dilates vascular smooth muscle and suppresses NO/cGMP signaling (Dae Gill Kang et al. (2005), *Eur. J. Pharmacol.*, 524:111-119).

While β-PGG is biosynthesized in plants predominantly, its α-anomer (α-PGG) having a chemical structure as shown below has been isolated as well.

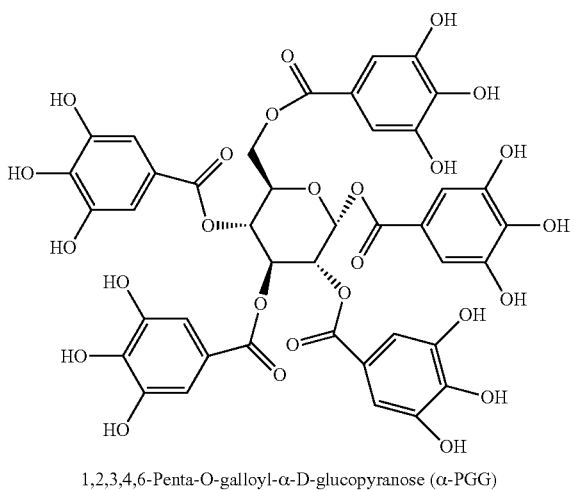 [SMILES: O=C(OC[C@H]1O[C@H](OC(=O)c2cc(O)c(O)c(O)c2)[C@H](OC(=O)c2cc(O)c(O)c(O)c2)[C@@H](OC(=O)c2cc(O)c(O)c(O)c2)[C@@H]1OC(=O)c1cc(O)c(O)c(O)c1)c1cc(O)c(O)c(O)c1]

1,2,3,4,6-Penta-O-galloyl-α-D-glucopyranose (α-PGG)

In addition to being prepared from natural sources, β-PGG and α-PGG as well as their analogues can be chemically synthesized and they are reported to activate insulin receptor to stimulate glucose transport in adipocytes and to function as an effective anti-diabetic drug (Yunsheng Li et al. (2005), *Biochem. Biophys. Res. Commun.*, 336:430-437; Yulin Ren et al. (2006), *J. Med. Chem.*, 49 (6):2829-2837; and US 20060058243 A1). In addition, US 20080149299 A1 discloses methods for the separation and/or purification of the α- and/or β-form of PGG without the need for HPLC. Reference is also made to Jinhui Zhang et al. (2009), *Pharm. Res.*, 26 (9): 2066-2080, which provides a thorough review of the biological activities and preparation of PGG.

In this invention, the applicants screened forty eight compounds isolated from plants commonly used in Chinese medicine for their activity to inhibit or prevent biofilm formation by microorganisms. The applicants surprisingly found that β-PGG, either in a solution or coated on solid surfaces, inhibited biofilm formation by microorganisms, in particular *S. aureus*, through inhibiting bacterial attachment and PIA formation. In particular, β-PGG did not inhibit the growth of microorganisms, yet prevented biofilm formation on the treated surfaces, implicating that β-PGG is unlikely to induce drug-resistance. In addition, β-PGG has an $IB_{50}$ value (i.e., the concentration that inhibits 50% biofilm formation) of 3.6 μM, which is significantly lower than those of N-acetyl cysteine, iodoacetamide, and N-phenyl maleimide, which are all known to inhibit biofilm formation by *S. aureus*. Biochemical and scanning electron microscopy results reveal that β-PGG inhibits initial attachment of the bacteria to solid surface and the synthesis of polysaccharide intercellular adhesion (PIA), explaining how PGG inhibits biofilm formation. Besides, β-PGG is not toxic to human epithelial and fibroblast cells.

The applicants further surprisingly found that α-PGG also exhibited excellent anti-biofilm activity as that of β-PGG. Based on these findings, PGG is expected to have great potential as a potent anti-biofilm agent in the fields of industry, manufacturing, building and construction, medical treatment, healthcare, water treatment, environmental protection, etc.

Accordingly, this invention provides an anti-biofilm composition comprising 1,2,3,4,6-Penta-O-galloyl-D-glucopyranose (PGG).

According to this invention, the term "1,2,3,4,6-Penta-O-galloyl-D-glucopyranose" or its abbreviation "PGG" includes:

(1) the β-form (β-anomer) of the PGG, i.e., β-PGG;
(2) the α-form (α-anomer) of the PGG, i.e., α-PGG;
(3) an analogue of the α- or β-PGG; and
(4) a mixture containing at least two of the α-PGG, the β-PGG and the analogue of the α- or β-PGG.

According to this invention, the analogue of the α- or β-PGG is one in which at least one of the glucose moiety of the PGG is substituted by other sugars such as hexoses, pentoses or tetroses. Hexoses that may be used include, but are not limited to, galactose, mannose, idose, talose, altrose, allose, gulose, fructose, or the like. Pentoses that may be used include, but are not limited to, xylose, ribose, arabinose, and lyxose. Tetroses that may be used include, but are not limited to threose and erythrose.

The PGG analogues as disclosed in Yulin Ren et al. (2006), supra, and those disclosed in US 20080249299 A1 may also be used in this invention.

When the anti-biofilm composition comprises a mixture containing at least two of the α-PGG, the β-PGG and the analogue of the α- or β-PGG, one of the components contained therein may be present in an amount of 50% or more of the mixture.

In a preferred embodiment of this invention, the anti-biofilm composition comprises the β-PGG.

In another preferred embodiment of this invention, the anti-biofilm composition comprises the α-PGG.

In yet another preferred embodiment of this invention, the anti-biofilm composition comprises a mixture of the α-PGG and the β-PGG. The mixture may contain 50% or more of the β-PGG and 50% or less of the α-PGG, or vice versa.

The anti-biofilm composition of this invention can be prepared using known methods. Generally, PGG is dissolved in a suitable solvent, such as water, buffer solutions, phosphate buffered saline, saline, or organic solvents such as DMSO, and may further comprise ingredients such as, but not limited to: antibiotics such as antibacterials and antifungals; anti-cancer drugs; binding, bonding or coupling agent, cross-linking agent; or a pH adjuster.

The anti-biofilm composition of this invention may further comprise one or more polymeric materials which facilitate dispersion of PGG to surfaces to be treated therewith, e.g., the inner and/or outer surfaces of medical devices. Preferably, the polymeric material may be a film-forming material that contributes to the formation of a coating or a thin film or layer on a substrate or surface treated with the composition of this invention.

According to this invention, the polymeric materials include, but are not limited to, polyaniline, polypyrrole, poly N-methylaniline (PNMA), chitosan, alginate, dextran, collagen, polyvinyl, polyethylene, polyurethane, polypropylene, silicone (e.g., silicone lassoers and silicone adhesives), poly(acrylic acid) (PAA), polymethacrylic acid, polymaleic acid, poly-(maleic acid monoester), poly(ethylene glycol) (PEG), polyaspartic acid, polyglutamic acid, aginic acid or pectimic acid, polycarboxylic acid anhydrides (e.g., polymaleic anhydride, polymethacrylic anhydride or polyacrylic acid anhydride), polyamines, polyethylene imine, polyvinylamine, polylysine, poly-(dialkylaminoethyl methacrylate), poly-(dialkylaminomethyl styrene), poly-(vinylpyridine), poly-(2-methacryloxyethyl trialkyl ammonium ion), poly-(vinylbenzyl trialkyl ammonium ions), poly-(N,N-alkylpyridinium ion), poly-(dialkyloctamethylene ammonium ion), polysulfonates, poly-(vinyl sulfonate), poly-(styrene sulfonate), collodion, nylon, rubber, plastic, polyesters, Dacron™ (polyethylene tetraphthalate), Teflon™ (polytetrafluoroethylene), latex, elastomers and Dacron (sealed with gelatin, collagen or albumin), cyanoacrylates, methacrylates, and derivatives thereof.

The polymeric film forming material as disclosed in US 20110076312 A1 may also be used in this invention. For example, the polymeric film forming material may be selected from the group consisting of aliphatic polyesters, poly(amino acids), copoly(ether-esters), polyalkylenes oxalates, polyamides, poly(ethylene glycol), poly(iminocarbonates), polyorthoesters, polyoxaesters, polyamidoesters, polyoxaesters containing amine groups, poly(anhydrides), polyphosphazene, polysaccharide gels and copolymers and blends thereof. Preferably, the polymeric film forming material is selected from homopolymers and/or copolymers of lactide, glycolide, epsilon-caprolactone, para-dioxanone, trimethylene carbonate, alkyl derivatives of trimethylene carbonate, monoglyceride polyesters, carboxymethyl cellulose hydrogels, and blends thereof. More preferably, the polymeric film forming material is homopolymer of lactide (PLA), or homopolymer of glycolide (PGA), or copolymer of PLA and PGA.

The composition according to this invention may form an anti-biofilm coating or thin film or layer on a site treated therewith. As used herein, the term "coating" or "thin film" refers to any temporary, semi-permanent or permanent layer, covering or surface. The term "coating" and the term "thin film" may be used interchangeably.

A coating can be a gas, vapor, liquid, paste, semi-solid or solid. In addition, a coating can be applied as a liquid and solidify into a hard coating. Examples of coatings include polishes, surface cleaners, caulks, adhesives, finishes, paints, waxes, and polymerizable compositions (including phenolic resins, silicone polymers, chlorinated rubbers, coal tar and epoxy combinations, epoxy resin, polyamide resins, vinyl resins, elastomers, acrylate and methacrylate polymers, fluoropolymers, polyesters and polyurethanes, latex). Silicone resins, silicone polymers (e.g., room-temperature-vulcanizing (RTV) polymers) and silicone heat cured rubbers are suitable coatings for use in the invention. A coating containing an anti-biofilm agent freely dispersed in a polymer binder is referred to as "onolithic" coating. Coatings can be biodegradable, ablative, or dissolvable, so that the dissolution rate of the matrix controls the rate at which anti-biofilm agents are delivered to the surface. Elasticity can be engineered into coatings to accommodate pliability, e.g., swelling or shrinkage, of the surface to be coated. Coatings can also be non-ablative, and rely on diffusion principles to deliver a separate anti-biofilm agent to the surface. Non-ablative coatings can be porous or non-porous. Coatings can be non-leaching and durable over extended time points.

The composition according to this invention may be incorporated into pools, fountains, aquariums and the like, whether they are constructed from cement, a plastic derivative or the like. Biofilm formation in such areas where water remains in a container is well known. Coating the surfaces or incorporating the composition of this invention may inhibit biofilm formation on such materials, thereby reducing cleaning time or chemicals used for sanitizing such containers. For fountains or pools frequented by the general public, use of the present invention could reduce infection transferred to persons from biofilm formation on those materials.

In one embodiment, the composition of the present invention may be applied to or incorporated into industrial surfaces, including metals, ceramics, thermoplastics or thermoset polymers, elastomers, PVC, glass or wood to prevent biofilm formation. Application to such surfaces may decrease infection by contact of individuals, and could thereby increase efficacy of production where fewer employees and customers suffer sickness due to infection by microorganisms that would otherwise adhere to and colonize on such surfaces. Moreover, products manufactured by equipment incorporating the compositions of the present invention into or onto the substrate are less likely to contain biofilms. For example, where products manufactured in the food packaging industry are coated with or incorporate (i.e., as a comonomer) compositions of the present invention, resistance to biofilm formation may be conferred to those products, thereby alleviating spoilage. Additionally, machinery used in the food packaging industry can benefit from coating with the composition of this invention, increasing efficiency by decreasing sanitizing time of machinery, and decreasing the instance of fouling of the foods processed by those machines. Furthermore, using the composition of this invention in the restaurant industry (e.g., countertops, flatware, silverware, dishes, tables, chairs, serving trays, etc.) on materials that come into contact with the food preparation process and where consumers are present could reduce the risk of food-borne or similar illness of customers and employees.

The composition of this invention may be incorporated into indoor paints, thus decreasing biofilm formation on surfaces using such paints. This could have a significant impact in decreasing infection from skin-contact interaction with those surfaces.

The composition of this invention may be employed in concrete structures used to house animals in the industrial setting. Biofilm formation in such structures is well known and is the cause of infection that compromises the health of livestock and fowl. Rendering surfaces of such structures, whether they be constructed of concrete, metal, wood or the like could significantly reduce the formation of biofilms and subsequently decrease the likelihood of infection in such settings. A decrease of infection of such livestock and fowl not only provides economic advantage, but also increases their safety for consumption by end users.

In addition, for household use, the composition of this invention can be incorporated into ointments to protect injured areas and to protect intact skin from prolonged microbial exposure. As an example, a topical pharmaceutical composition containing the anti-biofilm composition of this invention can inhibit the development of fungal infections like athlete's foot, in which the topical pharmaceutical composition can be prepared as a cream, an ointment, a powder or a spray. Other preparations can be used in moist areas to inhibit local yeast infections. Further, applying the anti-biofilm composition of this invention to materials used for fabricating menstrual tampons may inhibit the formation of those Staphylococci responsible for toxic shock syndrome.

The anti-biofilm composition of this invention may also be used in the preparation of wound care devices such as non-resorbable gauze/sponge dressing, hydrophilic wound dressing, occlusive wound dressing, hydrogel wound dressing, burn dressing, and spray-applicator for wound healing. Besides, the anti-biofilm composition of this invention may also be formulated in wound care ointments, gels, and lotions.

Formulation of such a preparation is consistent with the skill of ordinary practitioner in these arts.

The compositions of this invention can be formulated as a solution suitable for application to skin surfaces that will form a durable film that can remain in place over a sustained period of time. Such a solution could be applied to the hands of medical personnel underneath surgical gloves to reduce the contamination hazards from glove tears. Such a solution could also be applied to exposed skin surfaces, for example the uncovered face, of medical personnel in settings where contaminated splashes are likely.

Naturally derived processed materials commonly are positioned in the body in order to provide a structure for ingrowth of the patient's own tissues. Examples include demineralized bone materials and hydroxyapatite. These materials themselves are non-living and avascular. Colonization of these materials with microorganisms and biofilm formation can require their removal, reducing or ablating the ability of the patient to heal. Incorporating the compositions of the present invention into or onto substrates made of these materials can enhance their resistance to biofilm formation and its consequences. For example, solid articles such as reconstructive blocks of hydroxyapatite can be painted with a coating of the anti-biofilm composition of this invention for additional protection.

Implantable medical devices, using artificial materials alone or in combination with naturally-derived materials, can be treated with compositions of this invention either by surface coating or by incorporation. Metals may be suitably treated with surface coats while retaining their biological properties. Certain embodiments treated in this manner may be suitable for orthopedic applications, for example, pins, screws, plates or parts of artificial joints. Methods for surface treatment of metals for biological use are well-known in the relevant arts. Other materials besides metals can be treated with surface coats of compositions according to this invention as the medical application requires.

Implantable devices may comprise materials suitable for coating or incorporating the present invention into those surfaces with the compositions of this invention. Embodiments whose components may be coated with compositions of the present invention can include polymers, ceramics and other substances. Bioabsorbable materials such as poly(glycolic acid) and poly(lactic acid) polymers can be used to fabricate sutures and orthopedic devices. Those of ordinary skill in these arts will be familiar with techniques for incorporating the present invention onto the polymers used to shape formed articles for medical applications. Compositions of this invention may be incorporated into glues, cements or adhesives, or in other materials used to fix structures within the body or to adhere implants to a body structure. Examples include poly(methyl methacrylate) and its related compounds, used for the affixation of orthopedic and dental prostheses within the body. The presence of the composition of this invention can decrease biofilm formation in those structures in contact with the glue, cement, or adhesive. A composition of this invention can coat or can permeate the formed article. By coating, the composition of this invention prevents and/or minimizes adherence and colonization of microorganisms responsible for biofilm formation.

In one embodiment, the composition of this invention can be applied onto or incorporated in certain medical devices that are intended to be left in position permanently to replace or restore vital functions. As an example, ventriculoatrial or ventriculoperitoneal shunts, and dialysis shunts may be coated with the composition of the present invention. Dialysis shunts are especially susceptible to the formation of biofilms and subsequent infection and may be a part of a lifelong process, making it desirable to prevent the attachment and colonization of microorganisms that can form biofilms.

Heart valves comprising artificial material are understood to be vulnerable to the dangerous complication of prosthetic valve endocarditis. Artificial heart valves coated with the compositions of the invention may reduce the incidence of primary and recurrent prosthetic valve endocarditis caused by biofilm formation. The compositions of this invention can be applied to the synthetic portions or the naturally-derived portions of heart valves.

Pacemakers and artificial implantable defibrillators commonly comprise metallic parts in combination with other synthetic materials. These devices may be coated with compositions of the invention to reduce biofilm formation, which necessitates removal and replacement of the medical device.

Devices implanted into the body either temporarily or permanently to pump pharmacological agents into the body can comprise metallic parts in combination with other synthetic materials. The device may be partially or entirely covered with the composition of this invention, thereby reducing the risk of contamination and subsequent infection.

Additionally, various vascular grafting prostheses and stents intended to bypass blocked arteries or substitute for damaged arteries may employ the composition of this invention. Vascular grafting prostheses, made of poly(tetrafluoroethylene), poly(ethylene terephthalate), expanded poly(tetrafluoroethylene) (e-PTFE), and related materials, are available for use on any major blood vessel in the body and may be coated with or covalently incorporate the composition of this present invention. Stents comprising metallic frames covered with vascular grafting prosthesis fabric are also available for endovascular application to repair damaged blood vessels and may also be coated.

Suture materials can also harbor infections. Sutures are commonly made of prolene, nylon or other mono-filamentous non-absorbable materials, and absorbable materials such as catgut and polyglycolic acid. Suture materials comprising the anti-biofilm composition of this invention would have increased resistance to infection, thereby increasing their efficacy and the recovery of a patient. Fabricating an absorbable or a nonabsorbable suture comprising the composition of this invention and which retains the handling and tensile characteristics of the material is within the skill of artisans in the field.

The composition of this invention may also find application as/in an oral formulation wherein the composition of this invention is formulated in a carrier, e.g., selected from films, tapes, gels, microspheres, lozenges, chewing gums, dentrifices and mouthwash.

According to this invention, this invention may be used in the preparation of a pharmaceutical composition for treating conditions/diseases associated with biofilms, including, but not limited to: wounds, cystic fibrosis, pneumonia, native valve endocarditis and otitis media.

According to this invention, wounds include, but are not limited to, a cutaneous abscess, surgical wound, sutured laceration, contaminated laceration, blister wound, soft tissue wound, partial thickness burn, full thickness burn, decubitus ulcer, stasis ulcer, foot ulcer, venous ulcer, diabetic ulcer, ischemic ulcer, pressure ulcer, or combinations thereof.

A pharmaceutical composition containing the composition of this invention may be made in the form of a dosage unit, including, but not limited to, a liquid or suspension, capsule, tablet, powder, or granule, with conventional additives such as lactose; mannitol, corn starch or potato starch; with binders such as crystalline cellulose, cellulose derivatives, acacia, corn starch or gelatins; with disintegrators such as corn starch, potato starch or sodium carboxymethylcellulose; and with lubricants such as talc or magnesium stearate. The pharmaceutical composition may also be formulated as an injection wherein saline, dextrose or water may be used as a suitable carrier.

According to this invention, the pharmaceutical composition may further comprise an antimicrobial agent which includes, but is not limited to, dispersinB®, iodoacetamide (IDA), N-acetylcysteine (NAC), N-phenyl maleimide (NPM), triclosan, antibiotics (such as rifampicin, cefamandole nafate and ciprofloxacin), oxacillin, clarithromycin, cefazolin, azithromycin, tobramycin, polymyxin, linezolid, colistin, gentamycin, vancomycin, daptomycin, tigecycline, nitrofurazone, bismuth-thiols (such as bismuth ethanedithiol (BisEDT)), chitosan, Epigallocatechin gallate (EGCG), sodium usnate, antineoplastic agents (such as 5-fluorouracil), detergents (such as SDS, benzalkonium chloride), chlorhexidine, chelating agents (such as EDTA), silver compounds, bacteriophage, antimicrobial enzymes (such as glucose oxidase and lactoperoxidase), sugar alcohols (such as xylitol), maleimides (such as N,N-(1,2 phenylene)dimaleimide (oPDM) and N-(1-pyrenyl)maleimide (PyrM)), cadexomer iodine, methylene blue, gentian violet, medium chain dextrans (such as honey), and mixtures thereof. Other examples will be readily apparent to those practitioners of ordinary skill in the art.

This invention also provides a method to prevent or inhibit adhesion and/or biofilm formation by a microorganism, comprising applying to a site in need of such treatment a composition containing PGG, in which the PGG has the same definition as described above.

According to this invention, the site may be a surface made of a metal or metal alloy material, a glass material, a ceramic material, a plastic material, a fiber, a rubber material, or combinations thereof.

In one embodiment of this invention, the site is a hydrophobic surface made of polystyrene, polycarbonate, polyethylene, polypropylene, polyester, polyurethane, polyvinyl chloride, silicon rubber, latex rubber, nylon, Teflon, polytetrafluorocarbons, polymethylmethacrylate, acrylic co-polymer, cellophane, Dacron, polysulfon, or combinations thereof.

In another embodiment of this invention, the site is a hydrophilic surface made of glass, ceramics, hydroxyapatite, hydrogel, stainless steel, titanium alloys, nickel alloy, platinum-Iridium, Co—Cr alloy, or combinations thereof.

In a further embodiment of this invention, the site is the inner and/or outer surface of a medical device.

The method of the invention may be used to minimize and, preferably, prevent the formation of biofilms in a variety of environments including, but not limited to, household, workplace, laboratory, industrial environment, aquatic environment (e.g., pipeline systems), medical devices including indwelling devices such as those defined herein, dental devices or dental implants, and animal body for example human body.

In a preferred embodiment, a device is coated, impregnated, or treated with a composition as described herein, for example, a medical device such as a catheter, for example an indwelling catheter such as a central venous catheter, a peripheral intravenous catheter, an arterial catheter, a peritoneal catheter, a hemodialysis catheter, an umbilical catheter, a percutaneous nontunneled silicone catheter, a cuffed tunneled central venous catheter, an endotracheal tube, a urinary catheter, a peritoneal catheter, a peripheral intravenous catheter and a central venous catheter or a subcutaneous central venous port.

The medical device may also be pacemakers, prosthetic heart valves, prosthetic joints, voice prostheses, contact lenses, a stunt, heart valve, penile implant, small or temporary joint replacement, urinary dilator, cannula, elastomer, intrauterine devices, catheter lock, a needle, a Leur-Lok™ connector, a needleless connector, a clamp, forceps, scissors, a skin hook, a tubing, a needle, a retractor, a scaler, a drill, a chisel, a rasp, a surgical instrument, a dental instrument, a tube, an intravenous tube, a breathing tube, a dental water line, a dental drain tube, a feeding tube, a bandage, a wound dressing, an orthopedic implant, or a saw.

Medical devices also include equipments in hospital rooms, operating rooms, emergency rooms, clinics, and bathrooms.

In a preferred embodiment, the method of treating at least one surface of a medical device comprises contacting a medical device with a composition according to the invention. As used herein, the term "contacting" includes, but is not limited to: coating, spraying, soaking, rinsing, flushing, submerging, and washing. A medical device is contacted with a composition according to this invention for a period of time sufficient so that a coating or thin film or layer that prevents or inhibits the formation of biofilm by microorganism(s) is formed on the treated surface of the medical device.

In addition to methods for preparing such devices, methods of treating wounds and oral infections are also aspects of the present invention.

Oral infections include microorganisms in the subgingival and supragingival plaque. Subgingival plaque comprising microorganisms can cause periodontal disease. The composition of this invention can be used in the treatment of dental plaque and periodontal diseases. Therefore, this invention also provides an oral health product for preventing and/or inhibiting the formation of a biofilm in an oral cavity, dental plaque and/or dental tartar, said oral health product comprising PGG, in which the PGG has the same definition as described above. In one embodiment of this invention, the oral health product is a mouth wash.

This invention also provides a substrate to which the composition of this invention is applied or attached. Preferably, the substrate is suitable for application to wounds or delivery to wound sites. Preferably, the substrate may be a dressing, for example, wound dressing. The dressing may comprise a fabric material or it may be a collagen-like material. The substrate may be in any suitable form for application to a wound, typically the substrate may be in the form of a hydrogel, colloid, ointment, cream, gel, foam or spray.

The present invention will be described in more detail with reference to the following examples, which are given for the purpose of illustration only and are not intended to limit the scope of the present invention in any way.

EXAMPLES

Materials and Methods
1. Chemicals:

1,2,3,4,6-Penta-O-galloyl-β-D-glucopyranose (β-PGG) was prepared and kindly provided by Ms. Wan-Chun Lai. Briefly, β-PGG was purified from 680 g *Eustigma oblongifolium* (Hamamelidecae), which was collected from Kaohsiung County, Taiwan. A voucher specimen (*Eustigma*-01) was deposited at the Graduate Institute of Natural Products, Kaohsiung Medical University, Taiwan. Dry stems of *E. oblongifolium* were extracted with methanol and ethyl acetate. The extract was purified by silica gel and Sephadex LH-20 chromatography. The structure and purity of β-PGG were verified by mass and NMR spectrometry (Takashi Tanaka et al. (2003), *J. Nat. Prod.*, 66 (6):759-763).

1,2,3,4,6-Penta-O-galloyl-α-D-glucopyranose (α-PGG) was prepared substantially according to the procedures as set forth in Yulin Ren et al. (2006), supra.

Polyaniline was prepared and kindly provided by Mr. Hong-Wei Yang. Polyaniline was prepared as follows: aniline (0.1 mole) was added into 200 mL 1 M $HCl_{(aq)}$ on an ice bath and under a nitrogen purge, followed by dropwise addition of an ammonium peroxysulfate solution (0.75 M). After 9 hr reaction, the resultant mixture was filtered and then thoroughly washed with 1M $HCl_{(aq)}$ and deionized water in sequence until the filtrate became colorless. The product thus collected was added into 1 M ammonia (500 mL) to effect doping. 24 hours later, the resultant mixture was thoroughly washed with deionized water until the filtrate became neutral, followed by vacuum drying, thus giving a final product in powder form. The final product was identified to have the following structural formula:

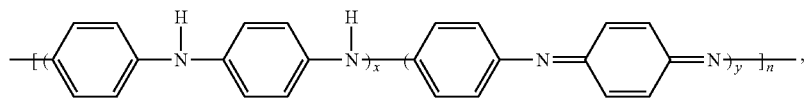

with a molecular weight ranging from 10000~15000 as measured by Gel Permeation Chromatography (GPC). The polyaniline polymer thus obtained was dissolved in dimethyl sulfoxide (DMSO) to give a stock concentration of 3 mg/mL (in DMSO).

Iodoacetamide (IDA), N-phenyl maleimide (NPM), and N-acetylcysteine (NAC) were purchased from Sigma-Aldrich (St. Louis, Mo., USA).

PGG (β- and α-forms) and NPM were dissolved in DMSO. IDA and NAC were dissolved in sterile distilled water. These chemicals were prepared as a 20 mM stock and stored at −20° C. prior to use.

2. Bacterial Strains and Culture Conditions:

*S. aureus* strains studied in this invention include: a biofilm-producing strain *S. aureus* SA113 (ATCC 35556) and an ica deletion mutant thereof (ATCC 35556Δica::tet) which does not produce PIA (Sarah E. Cramton et al. (1999), supra); clinical strains that are sensitive to methicillin (MSSA), including SA13, SA33, SA41, SA285, SA288 and SA289; and clinical strains that are resistant to methicillin (MRSA), including SA44, SA130, SA435, SA486, SA703 and SAChu.

In addition to the above *S. aureus* strains, *S. epidermidis* ATCC 35547 and *S. epidermidis* RP62A (ATCC 35984) were also studied for comparison. Besides, *S. carnosus* TM300 (Ralf Rosenstein et al. (2009), *Appl. Environ. Microbiol.*, 75 (3):811-822), which does not form biofilm, was used as a negative control.

All of the studied clinical strains, which were isolated from Chang Gung Memorial Hospital, Kwei-Shan, Taoyuan 333, Taiwan, were kindly provided by Dr. Chih-Jung Chen.

*S. aureus* SA113 (ATCC 35556) and *S. carnosus* TM300 were kindly provided by Prof. Friedrich Götz, Tubingen, Germany.

*S. epidermidis* ATCC 35547 and *S. epidermidis* RP62A (ATCC35984) were purchased from the Food Industry Development and Research Institute (FIRDI), Hsinchu, Taiwan.

All of the bacterial strains under test were cultured at 37° C. in a medium containing tryptic soy broth (Oxoid) plus 0.5% glucose, i.e., medium "TSBg".

3. Bacterial Cell Counting and Biofilm Quantification:

An overnight bacterial culture was 200-fold diluted with TSBg, and a 200 μL aliquot of the diluted culture was seeded into each well of 96-well polystyrene microtiter plates and incubated at 37° C. for a designated period of time. Cell growth was determined by measuring the absorbance at 578 nm ($A_{578}$) with a microtiter plate reader (SpectraMax 340, Molecular Devices). After washing with PBS twice to remove suspended cells, the wells were stained with 0.1% (w/v) crystal violet in 10% ethanol and then treated with 30% acetic acid in $dH_2O$, followed by detecting the absorbance at 595 nm ($A_{595}$) with the microtiter plate reader to quantify the amount of biofilm formed on polystyrene surface.

To count the number of viable cells, the removed suspended cells were suspended in PBS by pipetting, and the resultant cell suspension was sonicated and serially diluted and subsequently plated on TSBg agar plate for colony forming unit (CFU) counting according to a method described earlier (S. Schlag et al. (2007), *J. Bacteriol.*, 189:7911-7919).

To quantify the amount of biofilm formed on polycarbonate surface, a 13-mm-diameter polycarbonate disc (Thermanox, Nalgene Nunc International, Rochester, N.Y., USA) was placed in a well of a 24-well microtiter plate, followed by the addition of 1 mL aliquot of the diluted bacterial culture. After incubation at 37° C. for a designated period of time, viable cells were washed off the surface of the polycarbonate disc with PBS and counted as described above, while the PBS-washed polycarbonate disc was subjected to crystal violet staining for biofilm quantification as described above.

4. Screening of Compounds by Biofilm Assay:

An overnight culture of *S. aureus* SA113 was 200-fold diluted with TSBg, and a 200 μL aliquot of the diluted culture was seeded into each well of 96-well microtiter plates. Compounds purified from medicinal plants were added into each well at a designated concentration up to 60 mM. At 6 hours after seeding, the amounts of biofilms formed in the wells were determined by crystal violet staining as described above. Cells treated with either distilled water or DMSO were used as a control. The amount of biofilm formation by the control group was set as 100%. Each experiment was repeated at least three times, with n=6 for each sample tested. The concentrations of compounds that inhibited 50% biofilm formation ($IB_{50}$) were calculated based on logistic regression analysis results. Besides, the biofilm formation inhibition rate of a PGG-treated group was calculated using the following equation (1).

Biofilm formation inhibition rate(%)=[(A−B)/A]×100    (1)

wherein:
A=The mean $A_{595}$ value of the control group; and
B=The mean $A_{595}$ value of a PGG-treated group.

5. Adherence Assay:

β-PGG in different amounts (6.25 μM and 12.5 μM) was added at different time points (0, 0.5, 1, 1.5 and 2 hrs) after seeding *S. aureus* SA113 cells into either the wells of 96-well polystyrene microtiter plates or the wells of 24-well microtiter plates with polycarbonate discs placed in each well thereof. At 6 hours after seeding, the wells were subjected to crystal violet staining to determine the amounts of biofilm formed on the inner surfaces of the wells of polystyrene microtiter plates or on the polycarbonate discs.

Meanwhile, cells adhering to the polystyrene or polycarbonate surfaces were washed off with PBS at 60 min after seeding and stained with Syto 9 (Invitrogen), a green florescence dye that stains nucleic acids, followed by observation under a fluorescence microscope.

6. Quantification of PIA:

The amount of PIA was determined by chemiluminescence detection using horseradish peroxidase-conjugated streptavidin (Pierce) according to a method described elsewhere (S. Schlag et al. (2007), supra). Briefly, a tested bacterial strain prepared in TSBg broth was added with β-PGG at a designated concentration and then cultured in a 9 cm petri dish for 6 hrs. The bacterial cells grown in the petri dish were collected by scraping, followed by centrifugation, and the resultant cell pellets were redissolved by addition of 3 mL of 0.5 M EDTA (pH 8.0) for every gram (wet weight) of cell pellet, followed by boiling at 100° C. for 10 min. After centrifugation at 10,000 g for 30 min, the resultant supernatant was 100-fold diluted. An 80 µL aliquot of the diluted supernatant was incubated with 20 µL of proteinase K (10 mg/mL, in dH$_2$O) at 37° C. for 2 hrs, followed by blotting onto a PVDF membrane (Millipore) using a 96-well dot-blot apparatus. After blotting, the membrane was dried and soaked in a first blocking buffer (containing 3% bovine serum albumin (BSA) and 0.05% Tween-20 in PBS), followed by incubation at room temperature for 1 hr in the first blocking buffer containing 0.8 µg/mL wheat germ agglutinin conjugated with biotin (WGA-biotin, Sigma-Aldrich). After sequentially washing with the first blocking buffer and a second blocking buffer (containing 1% BSA and 0.05% Tween-20 in PBS), the membrane was incubated with horseradish peroxidase-conjugated streptavidin (Pierce) for 30 min, and washed 4 times with the first blocking buffer, followed by incubation with 1 mL of a substrate reagent (Luminol/Enhancer solution and Stable Peroxide solution, Pierce) at room temperature for 5 min. Thereafter, the membrane was detected by autoradiography using X-ray film, and the intensity of each spot formed on the X-ray film was quantified using a densitometer (LAS-3000, Fujifilm). The relative PIA amount produced by the tested bacterial strain was determined based on the detected intensity, with the amount of PIA from bacterial cells without PGG treatment being set as 100%.

To detect PIA in culture medium, the medium was concentrated using an Amicon-Ultra4 centrifuge filter (Millipore, Billerica, Mass., USA) prior to extraction.

7. Scanning Electron Microscopy (SEM):

*S. aureus* SA113 cells were grown on polycarbonate discs in the presence or absence of 3.13 µM β-PGG. After 6 hours incubation, the discs were washed three times with PBS to remove planktonic cells and then prepared for SEM examination as described elsewhere (Guo-Xian Wei et al. (2006), supra). The samples thus prepared were observed using a Hitachi S-5000 scanning electron microscope.

8. Detection of icaA Expression by Real-time Reverse Transcription Polymerase Chain Reaction (RT-PCR):

Bacterial cells were treated with 0.5 mg/mL lysostaphin (Sigma-Aldrich) at 37° C. for 15 min, and total bacterial mRNA was isolated and purified using a TRIzol reagent (Invitrogen) according to the manufacturer's instructions, followed by quantification of icaA expression by real-time RT-PCR (LightCycler, Roche, Mannheim, Germany). The icaA mRNA was reverse-transcribed and amplified using primers A1 (5'-gtgcagttgtcgacgttggctact-3') (SEQ ID NO:1) and B1 (5'-ttgagcccatctcacgcgttgc-3') (SEQ ID NO:2) that were designed based on the sequence of the icaA gene (Gene ID:3921484). The gyrB mRNA, which was used as an internal control to normalize the amount of icaA mRNA, was reverse transcribed and amplified using primers F1 (5'-acggataacggacgtggtatccca-3') (SEQ ID NO:3) and R1 (5'-gccaccgccgaatttaccacca-3) (SEQ ID NO:4) that were designed based on the sequence of the gyrB gene (Gene ID:2859950). Amplified PCR products were detected using a Light Cycler-RNA Amplification Kit Cyber Green 1 (Roche, Mannheim, Germany), starting with a cycle of denaturation at 95° C. for 5 min, then running for 45 cycles as follows: at 95° C. for 30 sec, 62° C. for 30 sec and 72° C. for 20 sec. To monitor the specificity of RT-PCR reaction, the PCR products were analyzed by melting curve analysis.

9. Inhibition of *S. aureus* Biofilm Formation on β-PGG-coated Surfaces:

β-PGG (stock conc.: 8.89 µg/mL in DMSO) in various amounts was evenly mixed with a fixed amount of polyaniline (40 µL, 3 mg/mL in DMSO) so as to provide a 100 µL β-PGG/polyaniline mixture with a final β-PGG concentration of 0.47 µM, 0.94 µM, 1.89 µM, 3.78 µM, 4.73 µM or 5.67 µM. The resultant β-PGG/polyaniline mixture was coated on the inner surfaces of the wells of 96-well polystyrene microtiter plates in an amount of 100 µL per well. After β-PGG coating, the plates were dried in a vacuum chamber, followed by UV sterilization for 30 min. An overnight culture of *S. aureus* SA113 was 200-fold diluted with TSBg, and a 200 µL aliquot of the diluted culture was seeded into each well of the β-PGG-coated microtiter plates. After culturing at 37° C. for 24 hrs, the wells were washed twice with PBS, and then examined by safranin staining according to a method described earlier (Christine Heilmann et al. (1996), *Infect. Immun.*, 64 (1):277-282), so as to quantify the amount of biofilm formed on the β-PGG-coated polystyrene surface.

Meanwhile, 6-mm diameter silicon rubber discs, which were cut from a sheet of 2-mm thick silicon rubber with a paper punch, were also coated with the resultant β-PGG mixture in an amount of 100 µL per disc. After β-PGG coating, the silicon rubber discs each were sterilized under UV for 30 min and placed into a well of a 48-well microtiter plate that was seeded with 500 µL aliquot of the 200-fold diluted overnight culture of *S. aureus* SA113. After incubation at 37° C. for 24 hrs, each silicon rubber disc was subjected to safranin staining, so as to quantify the amount of biofilm formed thereon.

10. Cell Viability Assay:

Human HepG2 cells (ATCC HB-8065) and 293T cells (ATCC CRL-11268) were cultured in Dulbecco's modified Eagle's medium (DMEM) supplemented with 10% (v/v) fetal calf serum. Human MRC-5 cells (ATCC CCL171) and HEp-2 cells (ATCC CCL-23) were cultured in Eagle's minimum essential medium (MEM) supplemented with 10% fetal calf serum. These four human cell lines were seeded into 24-well polystyrene tissue culture plates at a cell density of 1×10$^5$ cells/500 µL medium per well, respectively. After incubation at 37° C. for 24 hrs, β-PGG was added into each well in various amounts (0, 6.25, 12.5, 25 and 50 µM). After 24 hr treatment of β-PGG, toxicity of β-PGG to these human cell lines was determined using the 3-(4,5-dimethylthiazol-2-yl)-2,5-diphenyltetrazolium bromide (MTT) method (Xiangshu Piao et al. (2008), supra). Additionally, toxicity of β-PGG to the 293T cells was also determined in medium containing 0% and 2% fetal calf serum. Cells treated with DMSO were used as a negative control.

11. Effects of α- and β-anomers of PGG on Bacterial Growth and Biofilm Formation:

In the wells of 96-well microtiter plates, *S. aureus* SA113 cells were cultured in TSBg broth in the presence of either β-PGG or α-PGG at different amounts (0, 1 and 10 μM). After incubation at 37° C. for 6 hrs, the cell density was determined by measuring the absorbance at 578 nm ($A_{578}$), and the amounts of biofilm were quantified by crystal violet staining, with the amount of biofilm formed by untreated bacterial cells being set as 100%. Each experiment was repeated three times, with n=6 for each sample tested.

Results

1. Screening of Compounds that Inhibit Biofilm Formation by *S. aureus*.

Forty eight compounds isolated from plants commonly used in Chinese medicine were screened for their activity to prevent biofilm formation by *S. aureus* SA113 at 6 hours after seeding the bacteria into the wells of 96-well polystyrene microtiter plates. According to the applicants' preliminary screening results, at a concentration of 100 μM, most of the tested compounds did not inhibit either bacterial growth or biofilm formation (data not shown).

However, referring to Table 1, several compounds, e.g., AN-3, AN-4, and AN-9, not only exhibited strong anti-biofilm activity, namely, reducing biofilm formation by >94%, but also inhibited bacterial growth by >60%. CSBM5-4 inhibited bacterial growth by 25% and prevented biofilm formation by 73%. β-PGG and CSBM4-2 reduced biofilm formation by 98% and 92%, and inhibited bacterial growth by 31% and 21%, respectively. At a concentration of 10 μM, β-PGG was the only compound that did not kill *S. aureus* SA113, but strongly inhibited biofilm formation—after 6 hr incubation, 10 μM β-PGG inhibited biofilm formation by 95%.

TABLE 1

Screening of compounds that inhibit biofilm formation by *S. aureus* SA113 in broth culture.

| | 100 μM | | 10 μM | |
|---|---|---|---|---|
| Compound | Growth (%) | Biofilm (%) | Growth (%) | Biofilm (%) |
| β-PGG | 69 ± 5* | 2 ± 0 | 109 ± 8 | 5 ± 1 |
| AN-3 | 15 ± 10 | 0 ± 2 | 28 ± 17 | 6 ± 4 |
| AN-4 | 40 ± 3 | 6 ± 3 | 37 ± 23 | 5 ± 9 |
| AN-9 | 9 ± 1 | 2 ± 2 | 112 ± 11 | 82 ± 18 |
| CSBM4-2 | 79 ± 19 | 8 ± 5 | 107 ± 1 | 87 ± 7 |
| CSBM5-4 | 75 ± 7 | 27 ± 32 | 101 ± 10 | 101 ± 7 |

*Values are expressed as mean percentages ± SD.

2. Comparison of the Efficacies of Anti-biofilm Compounds.

To determine the efficacy of β-PGG in inhibiting biofilm formation by *S. aureus* SA113, β-PGG was further compared with IDA, NPM and NAC, which all have been shown to prevent biofilm formation by microorganisms (Euan Burton et al. (2006), surpa; and C. Pérez-Giraldo et al. (1997), surpa). The obtained results are summarized in Table 2, in which NPM, IDA and NAC are shown to have an $IB_{50}$ value of 3.6, 41.9, 120.4 and 6381.8 μM, respectively, each value being significantly higher than that of β-PGG (3.6 μM).

TABLE 2

$IB_{50}$ values of different compounds on biofilm formation by *S. aureus* SA113.

| Compound | $IB_{50}$ (μM)[a] | Cell Growth (%)[b] |
|---|---|---|
| β-PGG | 3.6 | 100 |
| NPM | 41.9 | 66 |

TABLE 2-continued $IB_{50}$ values of different compounds on biofilm formation by *S. aureus* SA113.

| Compound | $IB_{50}$ (μM)[a] | Cell Growth (%)[b] |
|---|---|---|
| IDA | 120.4 | 50 |
| NAC | 6381.8 | 88 |

[a]$IB_{50}$ is defined as the concentration of a compound that inhibited 50% biofilm formation and was calculated from the results of the logistic regression equation.
[b]Percentage of growth as compared to the untreated control at the concentration of $IB_{50}$.

The efficacy of β-PGG in inhibiting biofilm formation by bacterial strains other than *S. aureus* SA113, including twelve clinical strains of *S. aureus*, was also evaluated, and the obtained results are summarized in Table 3. It can be seen from Table 3 that after 6 hr incubation, β-PGG at a concentration of 12.5 μM inhibited the capacity of most of the clinical strains to produce biofilm while not influencing their growth. Although β-PGG at a concentration of 12.5 μM did not effectively reduce the biofilm formation by clinical strains SA289, SA44, SA435 and SA703 as compared to other clinical strains tested, β-PGG at a concentration of 50 μM reduced the biofilm formation of these four clinical strains by 83-97% (data not shown). Besides, β-PGG at a concentration of 12.5 μM reduced the biofilm formation by *S. epidermidis* ATCC35547 and *S. epidermidis* RP62A by 90% and 35%, respectively.

TABLE 3

The efficacy of β-PGG in inhibiting the biofilm formation by twelve clinical strains of *S. aureus* and two *S. epidermidis* strains.

| | Growth ($A_{578}$) | | Biofilm ($A_{595}$) | |
|---|---|---|---|---|
| Bacterial strain | 0 μM[a] | 12.5 μM | 0 μM | 12.5 μM |
| *Staphylococcus* sp. | | | | |
| *S. aureus* SA113[b] | 0.68 ± 0.02[d] | 0.65 ± 0.03 | 6.31 ± 0.34 | 0.26 ± 0.28 |
| *S. carnosus* TM300[c] | 0.69 ± 0.02 | 0.70 ± 0.01 | 0.12 ± 0.01 | 0.10 ± 0.01 |
| *S. epidermidis* ATCC 35547 | 0.50 ± 0.01 | 0.42 ± 0.01 | 1.42 ± 0.09 | 0.15 ± 0.11 |
| *S. epidermidis* RP62A | 0.57 ± 0.09 | 0.56 ± 0.09 | 6.43 ± 0.04 | 4.18 ± 0.54 |
| MSSA | | | | |
| SA13 | 0.69 ± 0.09 | 0.67 ± 0.06 | 0.98 ± 0.13 | 0.12 ± 0.04 |
| SA33 | 0.79 ± 0.01 | 0.79 ± 0.04 | 0.80 ± 0.07 | 0.13 ± 0.03 |
| SA41 | 0.65 ± 0.02 | 0.61 ± 0.05 | 1.67 ± 0.27 | 0.36 ± 0.05 |
| SA285 | 0.56 ± 0.09 | 0.46 ± 0.03 | 0.86 ± 0.09 | 0.16 ± 0.02 |
| SA288 | 0.55 ± 0.01 | 0.50 ± 0.01 | 0.83 ± 0.02 | 0.10 ± 0.01 |
| SA289 | 0.77 ± 0.02 | 0.72 ± 0.07 | 1.16 ± 0.01 | 0.35 ± 0.01 |
| MRSA | | | | |
| SA44 | 0.66 ± 0.08 | 0.64 ± 0.04 | 1.33 ± 0.01 | 0.46 ± 0.01 |
| SA130 | 0.61 ± 0.12 | 0.62 ± 0.17 | 3.05 ± 0.10 | 0.32 ± 0.04 |
| SA435 | 0.64 ± 0.10 | 0.67 ± 0.09 | 0.97 ± 0.09 | 0.46 ± 0.06 |
| SA486 | 0.76 ± 0.08 | 0.65 ± 0.02 | 1.94 ± 0.19 | 0.26 ± 0.07 |
| SA703 | 0.74 ± 0.10 | 0.70 ± 0.07 | 2.33 ± 0.02 | 0.88 ± 0.07 |
| SAChu | 0.56 ± 0.02 | 0.52 ± 0.04 | 8.06 ± 0.10 | 0.77 ± 0.11 |

[a]β-PGG concentration.
[b]*S. aureus* SA113, which is a biofilm-producing strain, is used as a positive control.
[c]*S. carnosus* TM300, which does not form biofilm, is used as a negative control.
[d]Values are expressed as mean ± SD.

In addition to *Staphylococcus* sp., β-PGG also exhibited potent to mild anti-biofilm activity to *Enterococcus faecalis* and *Acinetobacter baumannii* (data not shown).

3. Effects of β-PGG Upon Bacterial Growth and Biofilm Formation.

To determine the effect(s) of (β-PGG upon bacterial growth and biofilm formation, β-PGG in various amounts (final concentration: 0, 1.56, 3.13, 6.25, 12.5, 25 and 50 µM) was added into the culture of S. aureus SA113 during seeding into the wells of polystyrene microtiter plates, followed by incubation at 37° C. for 6 hrs or 24 hrs. Cell growth was determined by measuring the absorbance at 578 nm, and the amount of biofilm formed on polystyrene surface was determined at 595 nm after crystal violet staining. In addition to polystyrene surface, the effect of β-PGG in inhibiting biofilm formation on polycarbonate surface was also examined according to the procedures as described in the preceding section entitled "Materials and methods."

The obtained results reveal that after 6 hours incubation, β-PGG at concentrations below 50 µM did not affect the viability of S. aureus SA113 cultured in the wells of polystyrene microtiter plates (FIG. 1, panel A). However, β-PGG at concentrations of 6.25 and 12.5 µM inhibited biofilm formation on polystyrene surface by 93% and 96%, respectively; and at 25 µM, the inhibition increased to 97% (FIG. 1, panel B, black bar). When the incubation time was extended to 24 hrs, the inhibition persisted and the amounts of biofilm detected after 24 hr incubation (FIG. 1, panel B, white bar) were approximately equal to those observed after 6 hr incubation.

β-PGG was also potent in inhibiting biofilm formation on polycarbonate surface. After 6 hours incubation, β-PGG at concentrations of 6.25 and 12.5 µM inhibited biofilm formation by 75% and 96%, respectively; and at 25 µM, the inhibition increased to 99% (FIG. 1, panel C, black bar). In addition, similar levels of inhibition by β-PGG on polycarbonate surface were observed when the incubation time was extended to 24 hrs (FIG. 1, panel C, white bar).

4. Prevention of Bacterial Adherence to Solid Surface by β-PGG.

Instead of inhibiting bacterial adherence to a solid surface during the initial stage of biofilm formation, PIA facilitates the accumulation and aggregation of bacterial cells in the biofilm. Consequently, a mutant that is defective in PIA synthesis, e.g., S. aureus SA113Δica, forms a thin biofilm in the wells of microtiter plates (Sarah E. Cramton et al. (1999), supra).

Figure 2:
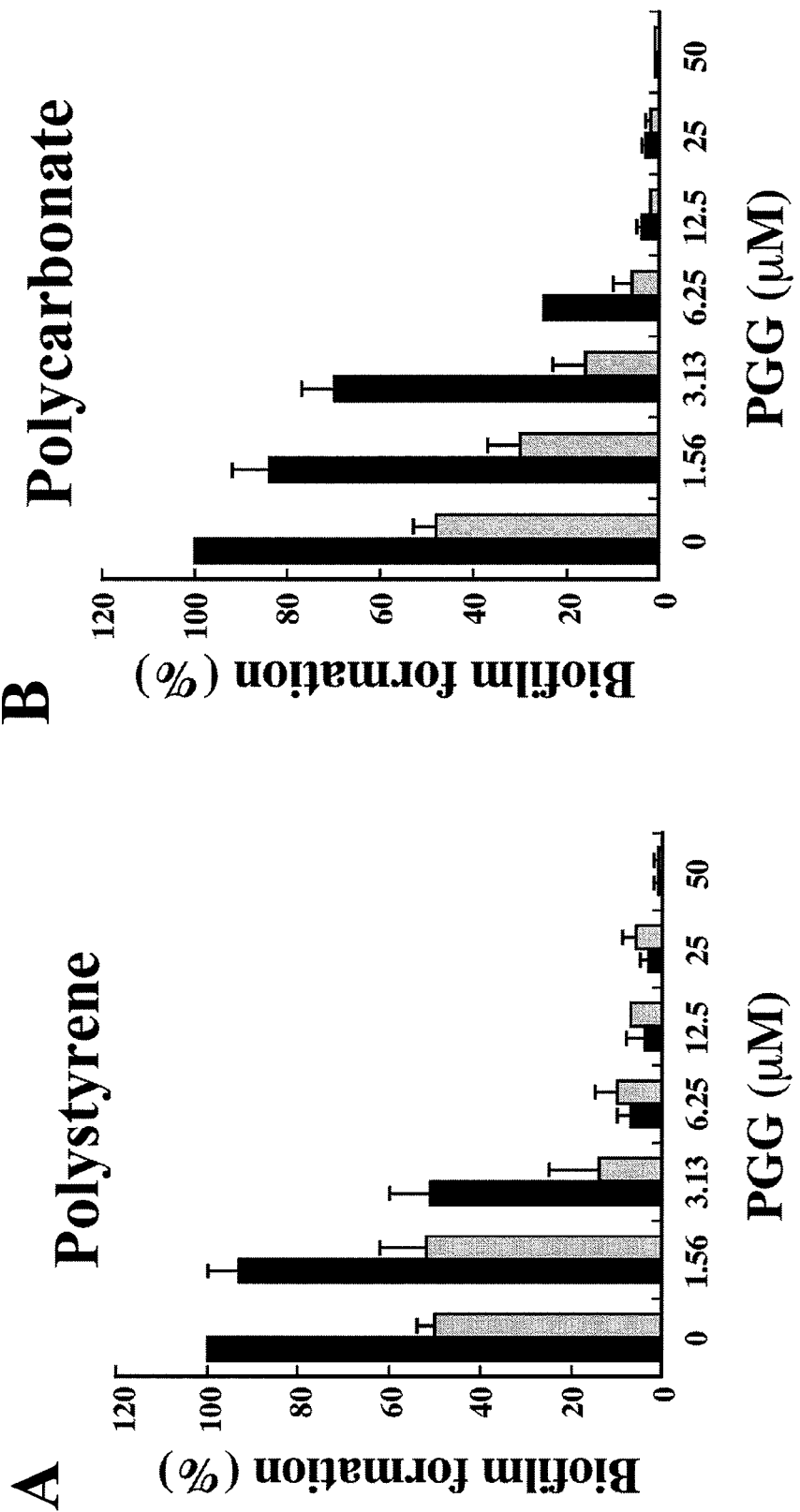
FIG. 2 shows the effects of β-PGG upon biofilm formation on polystyrene surface (panel A) and polycarbonate surface (panel B) by *S. aureus* SA113 (black bar) and its ica deletion mutant (ATCC 35556Δica::tet) (gray bar) after incubation at 37° C. for 6 hrs, in which the amount of biofilm formed by untreated bacterial cells was set as 100%; each experiment was repeated three times, with n=6 for each sample tested; and error bar represents standard deviation.
Figure 3:
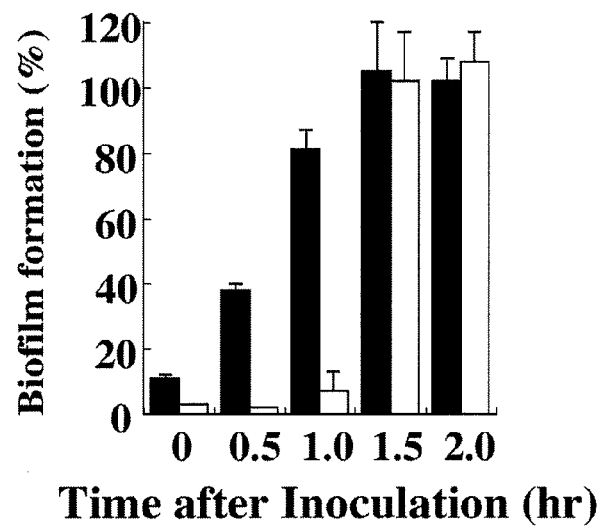
FIG. 3 shows the anti-adherence activity of β-PGG upon *S. aureus* SA113 cells seeded in the wells of 96-well microtiter plates, in which β-PGG at 6.25 μM (black bar) or 12.5 μM (white bar) was added into the wells at 0, 0.5, 1.0, 1.5 and 2 hours after inoculating *S. aureus* SA113 cells into the wells, respectively, and the amounts of biofilm formed on the inner surfaces of the wells were determined by crystal violet staining at 6 hours after inoculation; the amount of biofilm formed by bacterial cells treated with DMSO was set as 100%; each experiment was repeated three times, with n=6 for each sample tested; and error bar represents standard deviation.

As anticipated, the amount of biofilm formed by S. aureus SA113Δica on polystyrene surface was 50% less than that formed by S. aureus SA113 (FIG. 2, panel A). Although 1.56 µM β-PGG did not affect the biofilm formation by this mutant, 3.13 µMβ-PGG decreased the amount of biofilm by 72% (FIG. 2, panel A). Similar levels of inhibition were also observed on polycarbonate surface, in which this mutant produced about half of the amount of biofilm produced by S. aureus SA113 (FIG. 2, panel B); and at 3.13 µM and 12.5 µM, β-PGG decreased the amount of biofilm formed by S. aureus SA113Δica by 67% and 96%, respectively (FIG. 2, panel B). These results suggested that β-PGG probably inhibits the adherence of cells to a solid surface during the initial stage of biofilm formation. To verify this presumption, further experiments were conducted to study the kinetic of the anti-adherence activity of β-PGG.

β-PGG (6.25 µM or 12.5 µM) was added into S. aureus SA113 cultured in 96-well polystyrene microtiter plates at 0, 0.5, 1.0, 1.5 and 2 hr after bacterial inoculation, and the amounts of biofilm formed on the inner surfaces of the wells were determined by crystal violet staining at 6 hours after inoculation, with the amount of biofilm formed by bacterial cells treated with DMSO being set as 100%. Referring to FIG. 3, biofilm formation was reduced by 62% and 19% when 6.25 µM β-PGG (black bar) was added at 0.5 and 1 hr after bacterial inoculation, respectively. When 12.5 µM β-PGG (white bar) was added at 0.5 and 1 hr after bacterial inoculation, biofilm formation was reduced by more than 90%. However, biofilm formation was not inhibited if β-PGG was added at 1.5 and 2 hr after bacterial inoculation. These results reveal that the addition time of β-PGG is critical to the inhibition of biofilm formation, suggesting that β-PGG interferes with the initial attachment of S. aureus SA113 to polystyrene surface.

Figure 4:
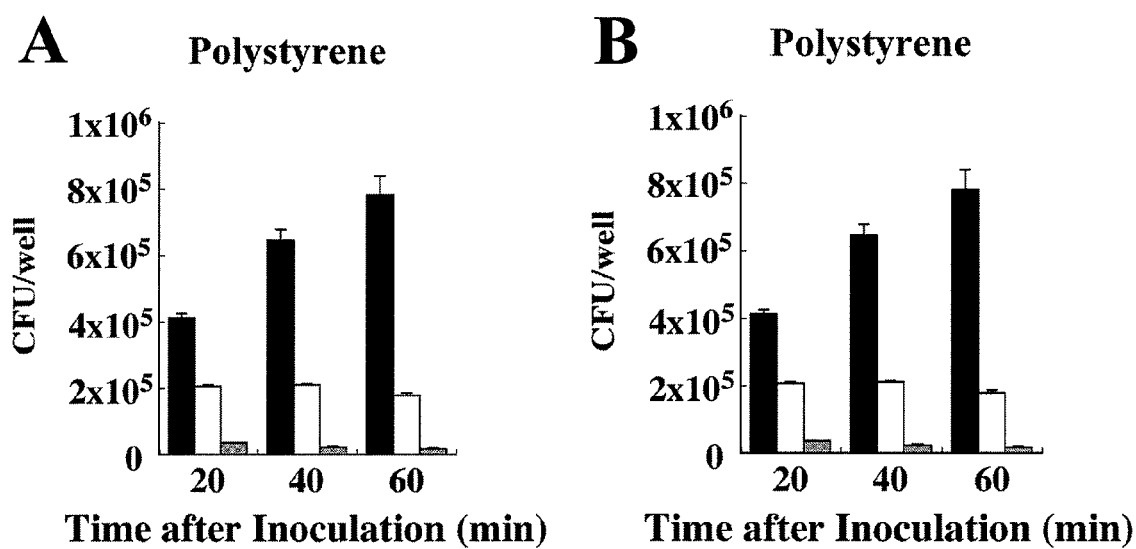
FIG. 4 shows the anti-adherence activities of β-PGG upon *S. aureus* SA113 cells grown on polystyrene surface (panel A) or polycarbonate surface (panel B), in which the bacterial cells were treated with β-PGG at 0 μM (black bar), 6.25 μM (white bar) and 12.5 μM (gray bar) for 20, 40 and 60 min, respectively, and the bacterial cells adhered to the polystyrene surface (panel A) or the polycarbonate surface (panel B) were washed off and suspended in PBS, followed by plating on TSBg agar for colony forming unit (CFU) counting; each experiment was repeated three times, with n=4 for each sample tested; and error bar represents standard deviation.

In addition to biofilm formation, the number of cells attached to polystyrene surface and polycarbonate surface were also counted. Subsequent to the incubation of S. aureus SA113 cells with β-PGG (0 µM, 6.25 µM or 12.5 µM) for 20, 40 and 60 min, cells adhered to the polystyrene surface or polycarbonate surface were washed and suspended in PBS, followed by plating on TSBg agar for CFU counting. After incubation on polystyrene surface for 20, 40 and 60 min, the number of cells counted for the DMSO-treated control (i.e., 0 µM β-PGG) was $4.1\times10^5$, $6.4\times10^5$ and $7.8\times10^5$ CFU, respectively (FIG. 4, panel A, black bars). However, β-PGG at 6.25 µM reduced the number of cells attached to polystyrene surface to $2.1\times10^5$, $2.05\times10^5$ and $1.8\times10^5$ CFU, respectively (FIG. 4, panel A, white bars), and β-PGG at 12.5 µM decreased the number of cells to $3.7\times10^4$, $2.3\times10^4$ and $1.7\times10^4$ CFU, respectively (FIG. 4, panel A, gray bars).

Similar inhibition was also observed on polycarbonate surface, in which after incubation for 20, 40 and 60 min, the number of cells adhered to polycarbonate surface in the DMSO-treated control was $7\times10^5$, $1.1\times10^6$ and $2\times10^6$ CFU, respectively (FIG. 4, panel B, black bars); β-PGG at 6.25 µM reduced the number of cells attached to the polycarbonate surface to $2.9\times10^5$, $2.3\times10^5$ and $3.5\times10^5$ CFU, respectively (FIG. 4, panel B, white bars); and β-PGG at 12.5 µM decreased the number of cells to $1.0\times10^5$, $8\times10^4$ and $5\times10^4$ CFU, respectively (FIG. 4, panel B, gray bars).

The cells adhering to the polystyrene surface and polycarbonate surface after treatment with 0 µM, 6.25 µM and 12.5 µM β-PGG for 60 min were also examined under a fluorescent microscope after Syto 9 staining. As evident from FIG. 5, β-PGG treatment significantly reduced the number of cells attached to polystyrene and polycarbonate surfaces.

5. Inhibition of PIA Synthesis by β-PGG.

Figure 6:
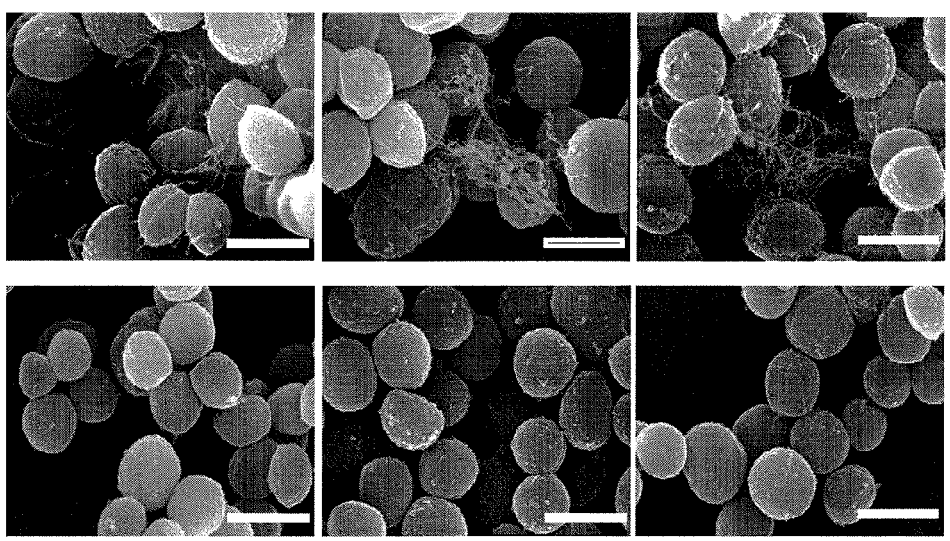
FIG. 6 shows scanning electron micrographs of *S. aureus* SA113 cells cultured on polycarbonate discs in the absence (upper three panels) or presence (lower three panels) of β-PGG at 3.13 μM for 6 hrs, in which images were taken at a magnification of 30,000× (scale bar=1.0 μm)

It is known that synthesis of EPS is essential to biofilm formation. According to the applicants' SEM study, after being cultured on polycarbonate discs for 6 hrs, S. aureus SA113 cells untreated with β-PGG produced filaments that form on polycarbonate surface a web structure that likely consists of PIA (FIG. 6, upper three panels) (Friedrich Götz (2002), supra; and Luanne Hall-Stoodley et al. (2008), *BMC Microbiol.*, 8:173). However, treating cells with 3.13 µM β-PGG caused the web structure to disappear (FIG. 6, lower three panels). Based on this finding, further experiments were conducted to analyze PIA production on bacterial surface after β-PGG treatment.

S. aureus SA113 cells were treated with β-PGG in various amounts (0, 3.13, 12.5 and 50 µM) for 6 hrs, and the amounts of PIA as extracted from either the cultured cells or the culture media were determined by chemiluminescence detection using conjugated WGA-biotin/HRP-streptavidin staining, with S. carnosus TM300 (a strain that does not produce biofilm) serving as a negative control (NC). Similar experiments were performed using four clinical isolates of S. aureus, namely MSSA strains SA13 and SA288, and MRSA strains SA44 and SA 130.

Figure 7:
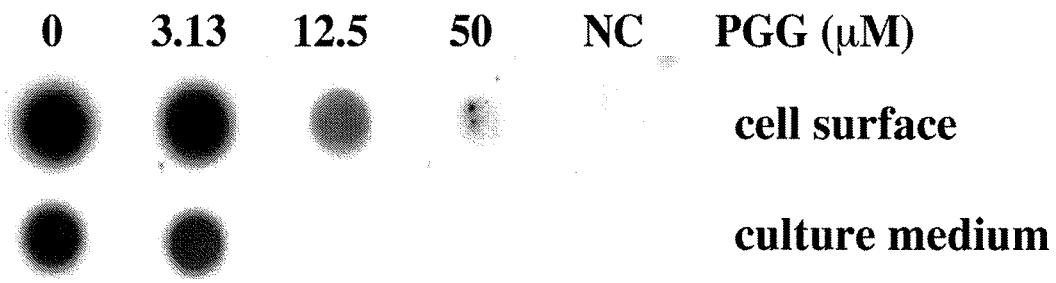
FIG. 7 shows the effect of β-PGG upon the production of polysaccharide intercellular adhesion (PIA) by *S. aureus* SA113 cells, in which the bacterial cells were treated with β-PGG in various amounts (0, 3.13, 12.5 and 50 μM) for 6 hrs, and the amounts of PIA as extracted from either the cultured cells (upper spot zone) or the culture media (lower spot zone) were determined by chemiluminescence detection using conjugated WGA-biotin/HRP-streptavidin, with *S. carnosus* TM300 (a strain that does not produce biofilm) serving as a negative control (NC)
Figure 8:
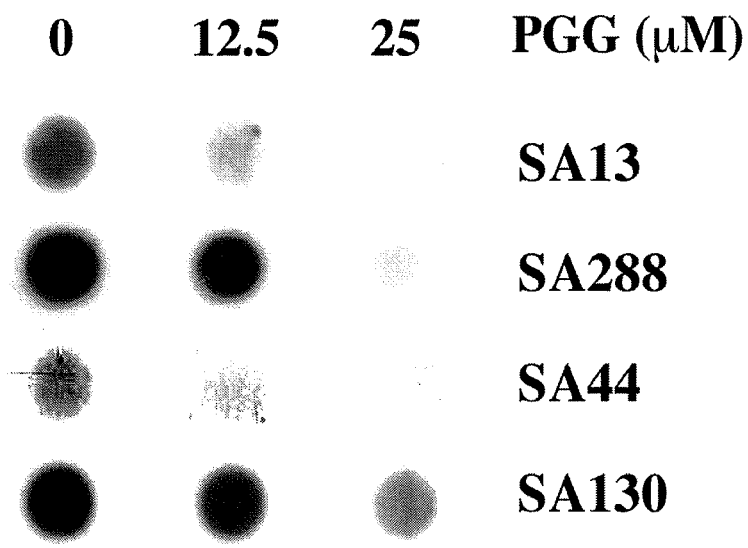
FIG. 8 shows the effects of β-PGG upon the PIA production by four clinical isolates of *S. aureus*, in which the bacterial cells were treated with β-PGG in various amounts (0, 12.5 and 25 μM) for 6 hrs, and the amounts of PIA extracted from the cultured cells were determined by chemiluminescence detection using conjugated WGA-biotin/HRP-streptavidin.

Extraction of PIA from bacterial cells cultured in TSBg that contained β-PGG in various amounts revealed that the PIA production was inhibited after β-PGG treatment (FIG. 7, upper spot zone). PIA released into the culture medium also decreased after β-PGG treatment in a dose-dependent manner (FIG. 7, lower spot zone). Similarly, β-PGG at 12.5 µM and 25 µM inhibited PIA production by the four tested clinical isolates of S. aureus (FIG. 8).

Figure 9:
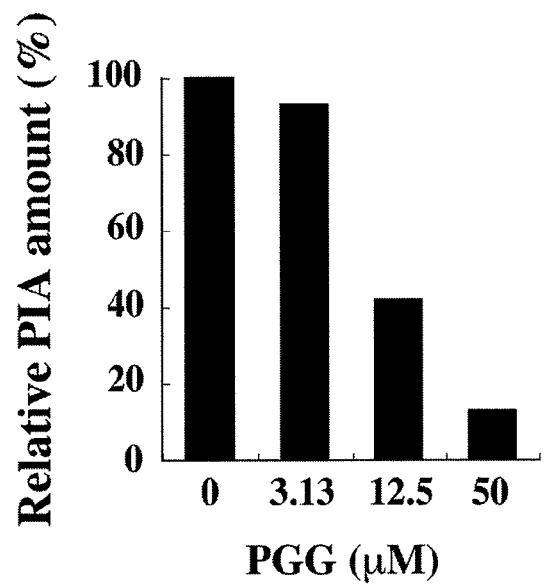
FIG. 9 shows the relative PIA amounts produced by *S. aureus* SA113 cells after treatment with β-PGG in various amounts (0, 3.13, 12.5 and 50 μM) for 6 hrs, in which the spots shown in the upper spot zone of FIG. 7 were quantified using a densitometer, with the amount of PIA from bacterial cells untreated with β-PGG being set as 100%.

The spots as shown in the upper spot zone of FIG. 7 were further quantified using a densitometer so as to determine the relative PIA amounts on the cell surfaces of S. aureus SA113 cells. Referring to FIG. 9, the amount of PIA formed on the cell surface decreased 7%, 58% and 87% after treatment with 3.13, 12.5 and 50 µM β-PGG, respectively.

To determine whether the β-PGG inhibition effected at the transcriptional level, total mRNAs were isolated from S. aureus SA113 cells after 5 hr treatment with β-PGG at various concentration (0, 3.13, 12.5 and 50 µM), and transcription of the icaA gene was analyzed by LightCycler quantitative RT-PCR. According to the results shown in FIG. 10, β-PGG at concentrations below 50 µM did not influence the transcription of icaA, indicating that β-PGG did not inhibit the transcription of the ica operon.

6. Inhibition of Biofilm Formation on Polystyrene and Silicon Rubber Surfaces by β-PGG.

Figure 11:
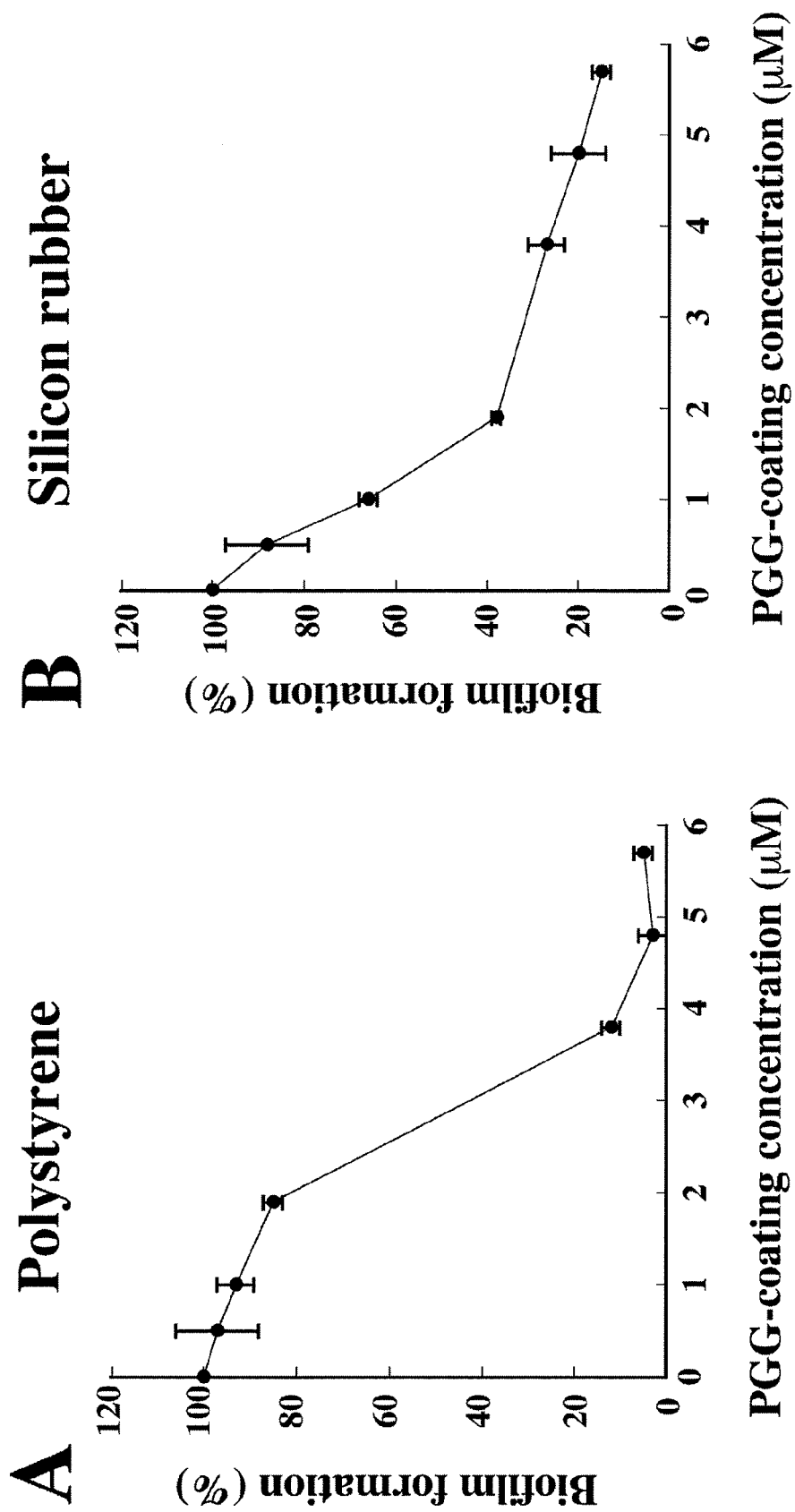
FIG. 11 shows the results of biofilm formation by *S. aureus* SA113 cells on β-PGG-coated surfaces, in which β-PGG was coated on the inner surfaces of the wells in a polystyrene microtiter plate (panel A) or on the surfaces of silicon rubber discs (B) using polyaniline as a carrier, followed by 24 hr incubation with *S. aureus* SA113 cells, and the amounts of biofilm formed on the polystyrene surface or the silicon rubber surface were quantified by safranin staining, with the amount of biofilm formed on untreated surfaces being set as 100%; each experiment was repeated three times, with n=4 for each sample tested; and error bar represents standard deviation.

Wells in 96-well polystyrene microtiter plates were coated with 0.5~5.7 µM β-PGG. The inhibition of biofilm formation by β-PGG was examined by safranin staining. The obtained results reveal that biofilm formation was slightly affected when the wells were coated with β-PGG at a concentration of 1.9 µM or lower (FIG. 11, panel A). However, the amount of biofilm decreased by more than 90% when the wells were coated with β-PGG at a concentration higher than 3.8 µM (FIG. 11, panel A).

β-PGG was also coated on the surface of silicon rubber, a material commonly found in catheters. The obtained results reveal that coating with 1.9 µM β-PGG inhibited biofilm formation by 62% (FIG. 11, panel B). When reaching a concentration of 5.7 µM, β-PGG inhibited biofilm formation by 85% (FIG. 11, panel B).

7. Toxicity of β-PGG to Human Cells.

Figure 12:
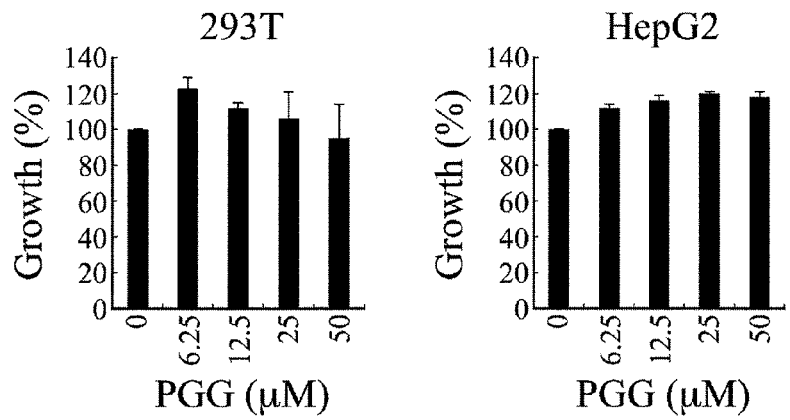
FIG. 12 shows the toxicity of β-PGG to human cells, in which human 293T, HepG2, HEp-2 and MRC-5 cells were incubated in culture medium containing 10% fetal calf serum (panel A) at 37° C. for 24 hrs, followed by 24 hr treatment of β-PGG in various amounts (0, 6.25, 12.5, 25 and 50 μM), and the cell viability was tested by the 3-(4,5-dimethylthiazol-2-yl)-2,5-diphenyltetrazolium bromide (MTT) method; the toxicity of β-PGG to the 293T cells cultured in medium supplemented with fetal calf serum at a concentration of 2% (panel B) or 0% (panel C) was also analyzed; the detected values from DMSO-treated cells were set as 100%; each experiment was repeated three times, with n=3 for each sample tested; and error bar represents standard deviation.
Figure 12:
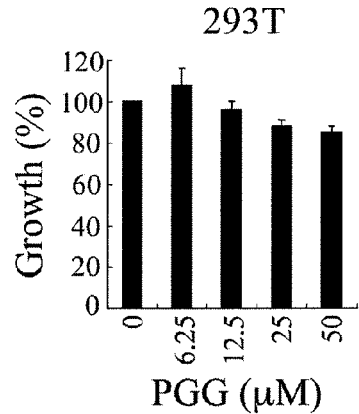
Figure 12:
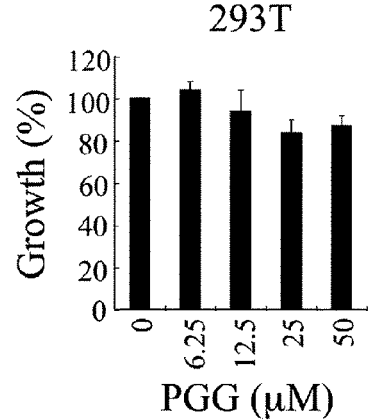

Toxicity of β-PGG to human 293T, HepG2, HEp-2 and MRC-5 cells was tested using an MTT-based colorimetric method ((Xiangshu Piao et al. (2008), supra). According to the obtained results, β-PGG did not affect the viability of 293T, HepG2, HEp-2, and MRC-5 cells at concentrations below 50 µM (FIG. 12, panel A). In addition, serum concentration in the culture medium appears to have no influence upon the toxicity of β-PGG toward the human 293T cells (FIG. 12, panels B and C).

Figure 13:
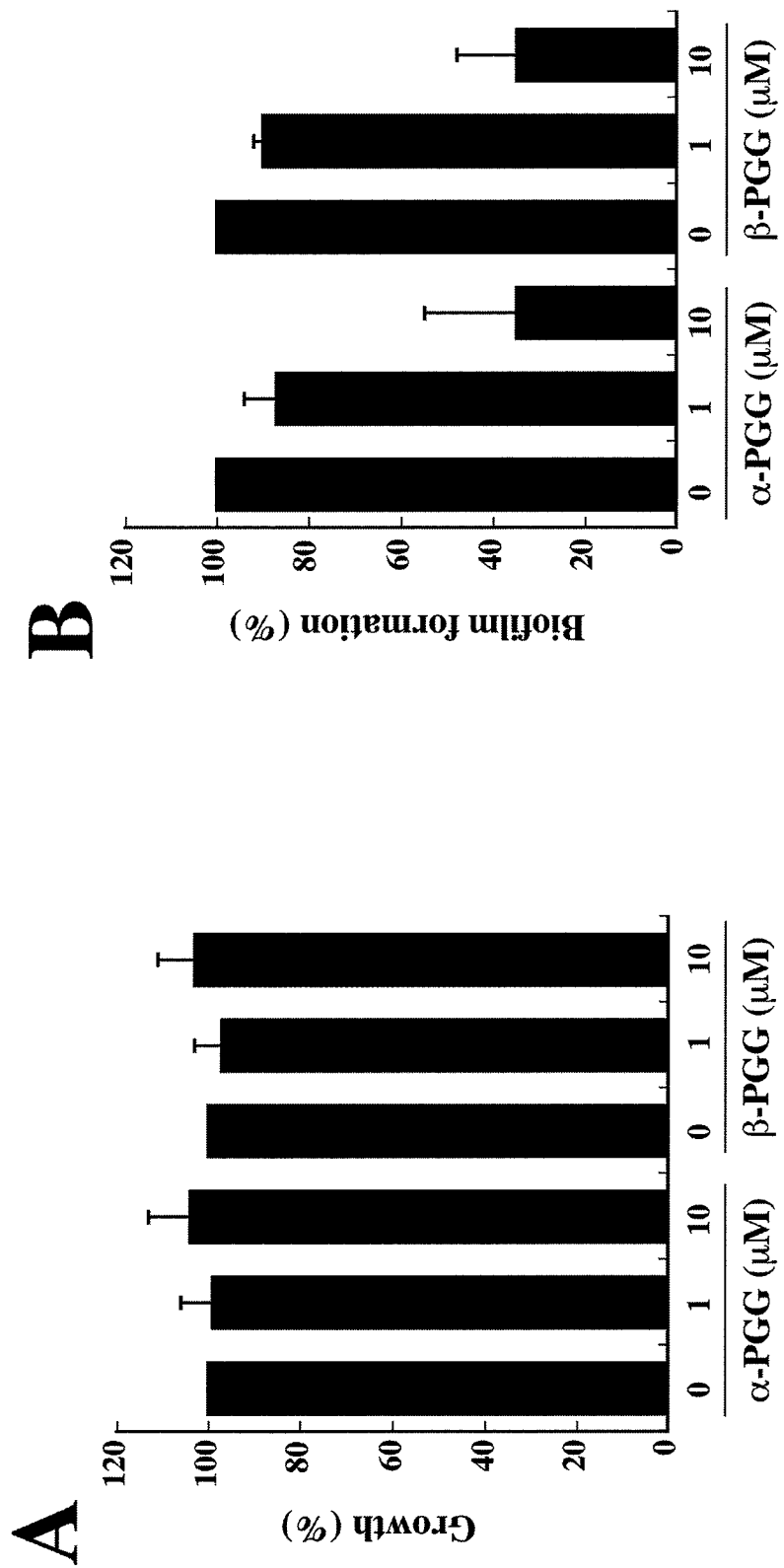
FIG. 13 shows the respective effects of β-PGG and its α-anomer (i.e., α-PGG) upon bacterial growth (panel A) and biofilm formation (panel B) by *S. aureus* SA113 cells after incubation at 37° C. for 6 hrs, in which the cell density was determined by measuring the absorbance at 578 nm ($A_{578}$); the amounts of biofilm were quantified by crystal violet staining, with the amount of biofilm formed by untreated bacterial cells being set as 100%; each experiment was repeated three times, with n=6 for each sample tested; and error bar represents standard deviation.

8. Effects of α- and β-anomers of PGG on Bacterial Growth and Biofilm Formation:

To determine the effects of α- and β-anomers of PGG on bacterial growth and biofilm formation, S. aureus SA113 cells cultured in 96-well microtiter plates were treated with α-PGG or β-PGG at different concentrations (0, 1, and 10 µM). It can be seen from FIG. 13 that after 6 hour incubation, both α-PGG and β-PGG at concentrations 1 µM and 10 µM did not affect the viability of S. aureus SA113 cells (FIG. 13, panel A). However, at a concentration of 1 µM, α-PGG and β-PGG reduced biofilm formation by 13% and 10%, respectively; and at a concentration of 10 µM, the reduction of biofilm formation by α-PGG and β-PGG increases to 65% and 65%, respectively (FIG. 13, panel B). The results indicate that the inhibitory effects of α-PGG and β-PGG on biofilm formation by S. aureus are similar.

Discussion

As a major cause of chronic infections, S. aureus forms biofilm on medical devices and implants (Rebecca A. Brady et al. (2008), *FEMS Immunol. Med. Microbiol.*, 52 (1):13-22). Because biofilm is extremely difficult to eliminate once formed on a surface, developing drugs that inhibit or eliminate S. aureus biofilms is vital to solving clinical problems caused by biofilm.

The applicants screened 48 compounds purified from medicinal plants and evaluated their efficacies in inhibiting biofilm formation by S. aureus. Amongst these compounds screened, only β-PGG did not kill S. aureus SA113 cells at concentrations below 50 µM (Table 1; and FIG. 1, panel A), yet reduced biofilm formation by 93% at 6.25 µM (FIG. 1, panel B). β-PGG also inhibited the biofilm formation by MSSA and MRSA clinical isolates and S. epidemidis strains (Table 3). The inhibitory effect of β-PGG on biofilm formation by these strains is apparently not correlated with susceptibility to clinically relevant antibiotics, such as methicillin (Table 3).

The applicants further examined how β-PGG inhibited biofilm formation on polystyrene and polycarbonate surfaces. These two materials are both hydrophobic, possibly explaining the observed finding that β-PGG is equally effective in preventing biofilm formation by S aureus SA113 on these two different materials (FIG. 1, panels B and C). It was further found that β-PGG inhibited bacterial attachment onto glass coverslips (data not shown), suggesting that β-PGG also prevents biofilm formation on hydrophilic surfaces.

In addition to the aforesaid surfaces, β-PGG inhibited biofilm formation on silicon rubber (FIG. 11, panel B), a material commonly used in catheters. These experimental results corroborate that β-PGG is potentially useful for coating medical devices to prevent biofilm formation.

Figure 5:
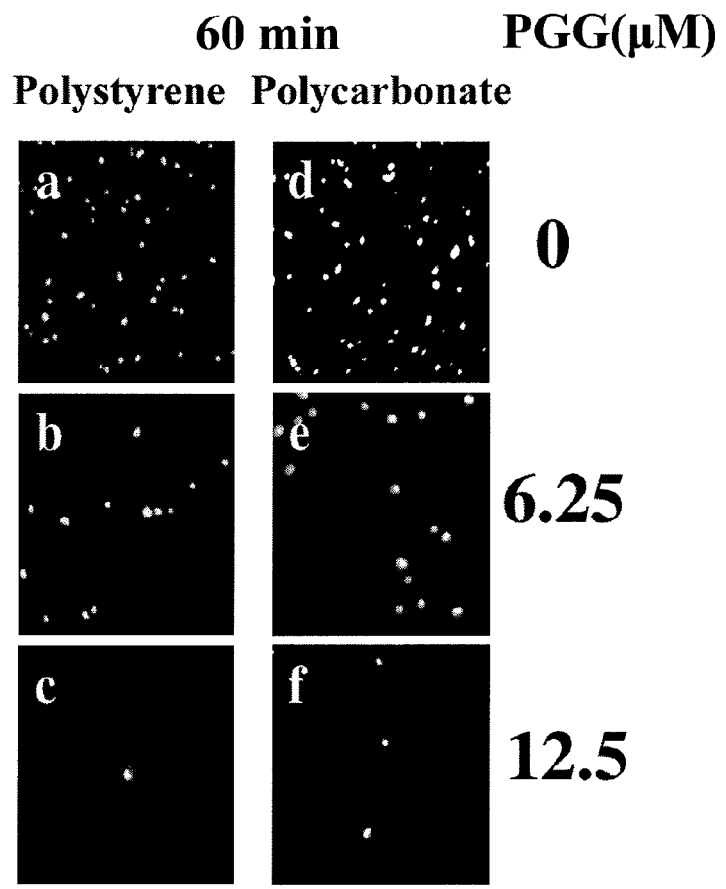
FIG. 5 is a photograph showing *S. aureus* SA113 cells adhered on polystyrene surface (panels a, b and c) or polycarbonate surface (panels d, e and f) after treatment with β-PGG at 0 μM (panels a and d), 6.25 μM (panels b and e) and 12.5 μM (panels c and f) for 60 min, as examined under a fluorescent microscope after Syto 9 staining.

According to the obtained experimental results, β-PGG likely inhibits the formation of S. aureus SA113 biofilm during the initial attachment stage because β-PGG is effective only when it is added into the culture medium within 1 hour after seeding (FIGS. 3-5). Because biofilm formation starts from cell attachment, the obtained results indicate that β-PGG inhibits the initial attachment of the cells to a solid surface. Additional evidence, which supports the notion that β-PGG inhibits initial cell attachment to a solid surface, comes from the results of experiments performed on a mutant strain, S. aureus SA113Δica. Although not producing PIA, which mediates cell-to-cell adhesion and cell aggregation during biofilm formation, this mutant strain can adhere to a solid surface but forms biofilm at a reduced level (Sarah E. Cramton et al. (1999), supra). Referring to FIG. 2, β-PGG inhibits biofilm formation by S. aureus SA113Δica on polystyrene and polycarbonate surfaces in a dose-dependent manner, implicating that β-PGG inhibits the primary attachment ability of this mutant strain.

Figure 10:
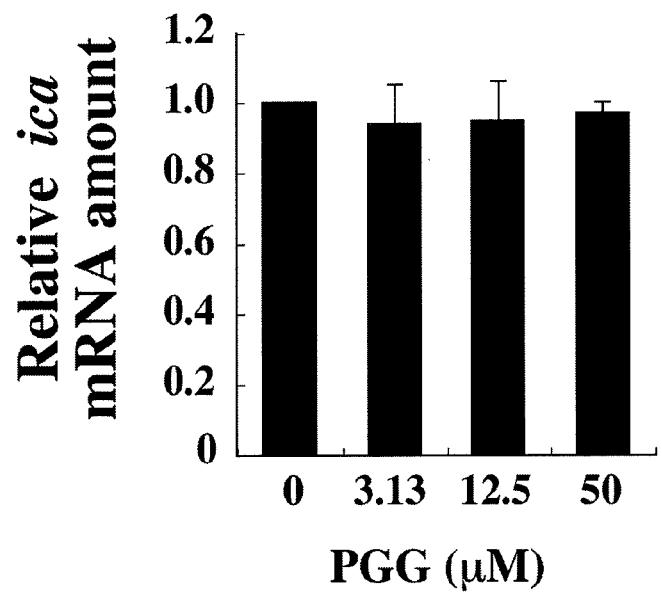
FIG. 10 shows the relative ica mRNA amounts produced by *S. aureus* SA113 cells, in which after treating the bacterial cells with β-PGG in various amounts (0, 3.13, 12.5 and 50 μM) for 5 hrs, total bacterial mRNA was isolated using TRIzol, and transcription of the icaA gene was analyzed by Light-Cycler quantitative RT-PCR; the gyrB gene was used as an internal control to normalize the expression level of the icaA gene; the detected amount of ica mRNA from bacterial cells untreated with β-PGG was set with a value of 1; each experiment was repeated three times, with n=4 for each sample tested; and error bar represents standard deviation.

According to the obtained experimental results, β-PGG not only inhibited the attachment of S. aureus strains to a solid surface at the onset of biofilm formation but also reduced the amount of PIA produced by S. aureus strains in a dose-dependent manner (FIGS. 7-10). The SEM data and the biochemical assay data reveal that PIA production by the biofilm cells is markedly reduced after β-PGG treatment (FIGS. 6-10). Such a decrease cannot be attributed to the possible promotion of PIA release from the cell surface to the medium by β-PGG because the amount of PIA is not increased in the culture medium after β-PGG treatment (FIG. 7). The reduced PIA synthesis is also not attributed to the repression of the ica operon at the transcriptional level since the quantitative RT-PCR results reveal that β-PGG treatment influences little of the amount of ica mRNA expressed by the cells (FIG. 10). It is presumed that β-PGG may affect the stability of enzyme(s) involved in the synthesis of PIA or intervene with the transportation of PIA to the cell surface. However, exactly how β-PGG affects PIA synthesis remains unclear.

Contamination of medical implants by microorganisms is a major risk of bloodstream infection and urinary tract infection (Dennis G. Maki and Paul A. Tambyah (2001), *Emerg. Infect. Dis.*, 7 (2):342-347). Therefore, strategies have been developed that involve coating clinical materials with antimicrobial substances, e.g., triclosan and dispersinB® (Rabih O. Darouiche et al. (2009), *J. Antimicrob. Chemother.*, 64:88-93), to prevent microbial colonization. Despite the anti-infection and anti-biofilm effects of coating, developing resistance to these substances by bacteria may cause adverse consequences. The experiments performed in this invention demonstrate the usefulness of polyaniline in coating β-PGG on polystyrene and silicon rubber and the effectiveness of the resultant coating in preventing biofilm formation.

As a natural product purified from a medicinal plant, β-PGG is commonly used in Chinese medicine. Although this compound is a strong antioxidant, its anti-oxidation activity may not be the only factor influencing biofilm formation. It was found in the study of this invention that treating *S. aureus* with other strong antioxidants, such as (−)-epigallocatechin gallate and ascorbic acid, does not influence biofilm formation (data not shown). The study of this invention further demonstrates that β-PGG is far more potent than three prior known anti-biofilm compounds, namely IDA, NAC and NPM (Table 2) and lacks toxicity to human epithelial and fibroblast cells at concentrations below 50 μM (FIG. 12). Moreover, the two anomers of PGG, i.e., β-PGG and α-PGG, share substantially the same anti-biofilm activity (FIG. 13). Based on these experimental results and in view of the structural similarity and biological properties of PGG anomers and their analogues, PGG, including its anomers and analogues, is highly promising for clinical use in preventing biofilm formation.

All patents and literature references cited in the present specification as well as the references described therein, are hereby incorporated by reference in their entirety. In case of conflict, the present description, including definitions, will prevail.

While this invention has been described with reference to the above specific embodiments, it will be understood that it is capable of further modifications and this application is intended to cover any variations, uses, or adaptations of the invention following, in general, the principles of this invention and including such departures from the present customary practice within the art to which this invention pertains and as may be applied to the essential features hereinbefore set forth, and as follows in the scope of the appended claims.

```
SEQUENCE LISTING
<110>  Liu, Shih-Tung

Lin, Mei-Hui

Chang, Fang-Rong

Hua, Mu-Yi

Yang, Hung-Wei

<120>  INHIBITION OF BIOFILM FORMATION BY
       1,2,3,4,6-PENTA-O-GALLOYL-D-
       GLUCOPYRANOSE

<130>  PE-42756-AM

<160>  4

<170>  PatentIn version 3.5
```

-continued

```
<210>  1

<211>  24

<212>  DNA

<213>  Artificial Sequence

<220>

<223>  RT-PCR primer for icaA mRNA

<400>  1 gtgcagttgt cgacgttggc tact                          24

<210>  2

<211>  22

<212>  DNA

<213>  Artificial Sequence

<220>

<223>  RT-PCR primer for icaA mRNA

<400>  2 ttgagcccat ctcacgcgtt gc                            22

<210>  3

<211>  24

<212>  DNA

<213>  Artificial Sequence

<220>

<223>  RT-PCR primer for gyrB mRNA

<400>  3 acggataacg gacgtggtat ccca                          24

<210>  4

<211>  22

<212>  DNA

<213>  Artificial Sequence

<220>

<223>  RT-PCR primer for gyrB mRNA

<400>  4 gccaccgccg aatttaccac ca                            22
```

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: synthetic RT-PCR primer for icaA mRNA

<400> SEQUENCE: 1
gtgcagttgt cgacgttggc tact                                    24

<210> SEQ ID NO 2
<211> LENGTH: 22
<212> TYPE: DNA
<213> ORGANISM: Artificial Sequence
<220> FEATURE:
<223> OTHER INFORMATION: synthetic RT-PCR primer for icaA mRNA

<400> SEQUENCE: 2
ttgagcccat ctcacgcgtt gc                                      22

<210> SEQ ID NO 3
<211> LENGTH: 24
<212> TYPE: DNA
<213> ORGANISM: Artificial Sequence
<220> FEATURE:
<223> OTHER INFORMATION: synthetic RT-PCR primer for gyrB mRNA

<400> SEQUENCE: 3
acggataacg gacgtggtat ccca                                    24

<210> SEQ ID NO 4
<211> LENGTH: 22
<212> TYPE: DNA
<213> ORGANISM: Artificial Sequence
<220> FEATURE:
<223> OTHER INFORMATION: synthetic RT-PCR primer for gyrB mRNA

<400> SEQUENCE: 4
gccaccgccg aatttaccac ca                                      22

We claim:

1. A method to prevent or inhibit cell adhesion and/or biofilm formation by a microorganism, comprising applying to a site in need of such treatment a composition containing a concentration of polyaniline and 1,2,3,4,6-penta-O-galloyl-D-glucopyranose (PGG) which is operative to inhibit cell adhesion and/or biofilm formation by a microorganism.

2. The method of claim 1, wherein the PGG is an α-anomer of PGG, a β-anomer of PGG, an analogue of PGG, or a mixture thereof.

3. The method of claim 1, wherein applying the composition to said site results in a coating or thin film or layer formed on said site so that formation of a biofilm on said site is prevented or inhibited.

4. The method of claim 1, wherein the composition further comprises an antimicrobial agent selected from the group consisting of iodoacetamide, N-acetylcysteine, N-phenyl maleimide, triclosan, rifampicin, cefamandole nafate, ciprofloxacin, oxacillin, clarithromycin, cefazolin, azithromycin, tobramycin, polymyxin, linezolid, colistin, gentamycin, vancomycin, daptomycin, tigecycline, nitrofurazone, bismuth ethanedithiol, chitosan, Epigallocatechin gallate, sodium usnate, 5-fluorouracil, detergents, chelating agents, silver compounds, bacteriophage, antimicrobial enzymes, sugar alcohols, maleimides, cadexomer iodine, methylene blue, gentian violet, medium chain dextrans, and mixtures thereof.

5. The method of claim 1, wherein said site is an industrial environment, a residential environment, a household environment, a medical environment, an aquatic environment, a laboratory, or a workplace.

6. The method of claim 1, wherein the site is a surface made of a material selected from the group consisting of metals or metal alloys, glass, ceramic, glaze ceramic, porcelain, wood, chrome, plastics, fibers, rubbers, and combinations thereof.

7. The method of claim 1, wherein the site is a hydrophobic surface made of polystyrene, polycarbonate, polyethylene, polypropylene, polyester, polyurethane, polyvinyl chloride, silicon rubber, latex rubber, nylon, Teflon, polytetrafluorocarbons, polymethylmethacrylate, acrylic co-polymer, cellophane, Dacron, polysulfon, or combinations thereof.

8. The method of claim 1, wherein the site is a hydrophilic surface made of glass, ceramics, hydroxyapatite, hydrogel, stainless steel, titanium alloys, nickel alloy, platinum-Iridium, Co—Cr alloy, or combinations thereof.

9. The method of claim 1, wherein the site is the inner and/or outer surface of a medical device.

10. The method of claim 1, wherein the microorganism is a Gram-positive or Gram-positive bacterial pathogen.

11. The method of claim 1, wherein the microorganism is a bacterial strain of *Staphylococcus* sp., *Enterococcus* sp., *Acinetobacter baumannii*, *Streptococcus* sp., *Pseudomonas* sp., *Escherichia coli*, *Helicobacter* sp., *Chlamydia* sp., *Clostridia* sp., *Haemophilus* sp., *Shigella* sp., *Bacillus* sp., *Neisseria* sp., *Mycobacterium* sp., *Francisella fularensis; Klebsiella* sp., *Yersinia* sp., *Propionibacterium* sp., *Burkholderia* sp., *Treponema* sp., *Enterobacter* sp., *Borrelia burgdorferi*, *Proteus mirabilis*, *Providentia sturtii*, *Serratia marcescens*, *Fusobacterium nucleatum*, *Aggregatibacter cictinontycetemcomitans*, *Salmonella* sp.; *Listeria* sp., *Campylobacter* sp., *Bacteriodes* sp., *Prevotella* sp., *Corynebacterium* sp., *Porphyromonas* sp., and *Peptostreptococcus* sp.

12. The method of claim 11, wherein the bacterial strain is a strain of *Staphylococcus* sp. selected form the group consisting of *Staphylococcus aureus* (*S. aureus*), *Staphylococcus epidermidis*, *Staphylococcus epitkonidis*, *Staphylococcus agalactiae*, *Staphylococcus saprophyticus*, *Staphylococcus haemolyticus*, *Staphylococcus warneri*, *Staphylococcus hominis*, *Staphylococcus simulans*, *Staphylococcus lugdunensis*, *Staphylococcus schleiferi*, *Staphylococcus capitis*, *Staphylococcus caprae*, *Staphylococcus pasteuri*, *Staphylococcus cohnii*, *Staphylococcus xylosus*, *Staphylococcus saccharolyticu*, and combinations thereof.

13. The method of claim 12, wherein the bacterial strain is a strain of *S. aureus*.

14. The method of claim 13, wherein the bacterial strain is a clinical strain of *S. aureus* that is sensitive to methicillin.

15. A method to inhibit the formation of a biofilm on at least a surface of a medical device, comprising treating the medical device with a composition containing polyaniline and 1,2,3,4,6-penta-O-galloyl-D-glucopyranose (PGG).

16. The method of claim 15, wherein the PGG is an α-anomer of PGG, a β-anomer of PGG, an analogue of PGG, or a mixture thereof.

17. The method of claim 15, wherein the medical device is one of the following: devices used in invasive surgical, therapeutic or diagnostic procedures; implantable medical devices; artificial hearts; artificial kidneys; orthopedic pins, plates and implants; catheters; urological, biliary or endotracheal tubes; peripherally insertable central venous catheters; dialysis catheters; long term tunneled central venous catheters; peripheral venous catheters; short term central venous catheters; arterial catheters; pulmonary catheters; Swan-Ganz catheters; urinary catheters; peritoneal catheters; long term urinary devices; tissue bonding urinary devices; artificial urinary sphincters; urinary dilators; ventricular or arteriovenous shunts; breast implants; penile prostheses; vascular grafting prostheses; heart valves; artificial joints; artificial larynxes; otological implants; vascular catheter ports; wound drain tubes; hydrocephalus shunts; pacemakers; and implantable defibrillators.

18. The method of claim 1, wherein the concentration of the PGG is equal to or less than 100 μM.

19. The method of claim 18, wherein the concentration of the PGG is equal to or less than 50 μM.

* * * * *